US006274870B1

(12) United States Patent
Kubo et al.

(10) Patent No.: US 6,274,870 B1
(45) Date of Patent: Aug. 14, 2001

(54) METHOD FOR SPECTROMETRICALLY MEASURING ISOTOPIC GAS AND APPARATUS THEREOF

(75) Inventors: Yasuhiro Kubo, Shiga; Katsuhiro Morisawa, Kyoto; Yasushi Zasu, Osaka; Eiji Ikegami, Kyoto; Kazunori Tsutsui, Osaka; Tamotsu Hamao, Kyoto; Masaaki Mori; Takashi Maruyama, both of Osaka, all of (JP)

(73) Assignee: Otsuka Pharmaceutical Co.,Ltd., Tokyo (JP)

( * ) Notice: Subject to any disclaimer, the term of this patent is extended or adjusted under 35 U.S.C. 154(b) by 0 days.

(21) Appl. No.: 09/303,427

(22) Filed: May 3, 1999

Related U.S. Application Data

(62) Division of application No. 08/849,351, filed as application No. PCT/JP96/02876 on Oct. 21, 1996.

(30) Foreign Application Priority Data

| Oct. 9, 1995 | (JP) | ................................................... 7-261744 |
| Oct. 9, 1995 | (JP) | ................................................... 7-261745 |
| Oct. 9, 1995 | (JP) | ................................................... 7-261746 |
| Oct. 11, 1995 | (JP) | ................................................... 7-263304 |
| Oct. 11, 1995 | (JP) | ................................................... 7-263305 |
| Dec. 1, 1995 | (JP) | ................................................... 7-314490 |
| Jan. 23, 1996 | (JP) | ................................................... 8-9545 |
| Mar. 14, 1996 | (JP) | ................................................... 8-58052 |

(51) Int. Cl.[7] ................................................... G01N 21/35
(52) U.S. Cl. ................... 250/339.13; 250/345; 250/343
(58) Field of Search ........................... 250/339.13, 345, 250/343

(56) References Cited

U.S. PATENT DOCUMENTS

| 4,247,773 | 1/1981 | Nexo et al. ........................ 250/339 |
| 5,146,294 | 9/1992 | Grisar et al. ...................... 356/435 |
| 5,486,699 | 1/1996 | Fabinski et al. .................. 250/345 |
| 5,543,621 | 8/1996 | Sauke et al. ...................... 250/339 |

FOREIGN PATENT DOCUMENTS

| 0 584 897 A1 | 3/1994 | (EP) . |
| 0 634 644 A1 | 1/1995 | (EP) . |
| 54-134088 | 10/1953 | (JP) . |
| 57-205056 | 6/1956 | (JP) . |
| 55-112546 | 8/1980 | (JP) . |
| 55-104740 | 11/1980 | (JP) . |
| 56-48822 | 11/1981 | (JP) . |
| 59-171836 | 9/1984 | (JP) . |
| 61-11634 | 1/1986 | (JP) . |
| 61-42220 | 9/1986 | (JP) . |
| 63-175847 | 9/1988 | (JP) . |

(List continued on next page.)

*Primary Examiner*—Constantine Hannaher
*Assistant Examiner*—Andrew Israel
(74) *Attorney, Agent, or Firm*—Finnegan, Farabow, Garrett, & Dunner L.L.P.

(57) ABSTRACT

A correction curve (FIG. 19) is prepared by plotting $^{12}CO_2$ concentrations and $^{13}CO_2/^{12}CO_2$ concentration ratios which are determined on the basis of a calibration curve and $^{13}CO_2$ and $^{12}CO_2$ absorbances of gaseous samples having the same $^{13}CO_2/^{12}CO_2$ concentration ratio but known different $^{12}CO_2$ concentrations. A gaseous test sample containing $^{13}CO_2$ and $^{12}CO_2$ as component gases is introduced into a cell, and spectrometrically measured. A $^{12}CO_2$ concentration of the gaseous test sample is determined by way of the spectrometric measurement. A concentration ratio correction value is obtained on the basis of the correction curve and the $^{12}CO_2$ concentration of the gaseous test sample thus determined. A measured $^{13}CO_2/^{12}CO_2$ concentration ratio is divided by the concentration ratio correction value thus obtained for correction of the $^{13}CO_2/^{12}CO_2$ concentration ratio. Thus, the measurement accuracy of the concentration ratios of the component gases can be improved.

14 Claims, 24 Drawing Sheets

FOREIGN PATENT DOCUMENTS

| | | |
|---|---|---|
| 1-61647 | 4/1989 | (JP) . |
| 2-42338 | 2/1990 | (JP) . |
| 4-160349 | 6/1992 | (JP) . |
| 4-364442 | 12/1992 | (JP) . |
| 5-142146 | 6/1993 | (JP) . |
| 5-296922 | 11/1993 | (JP) . |
| 7-190930 | 7/1995 | (JP) . |
| WO 93/06460 | 4/1993 | (WO) . |

F I G. 10A
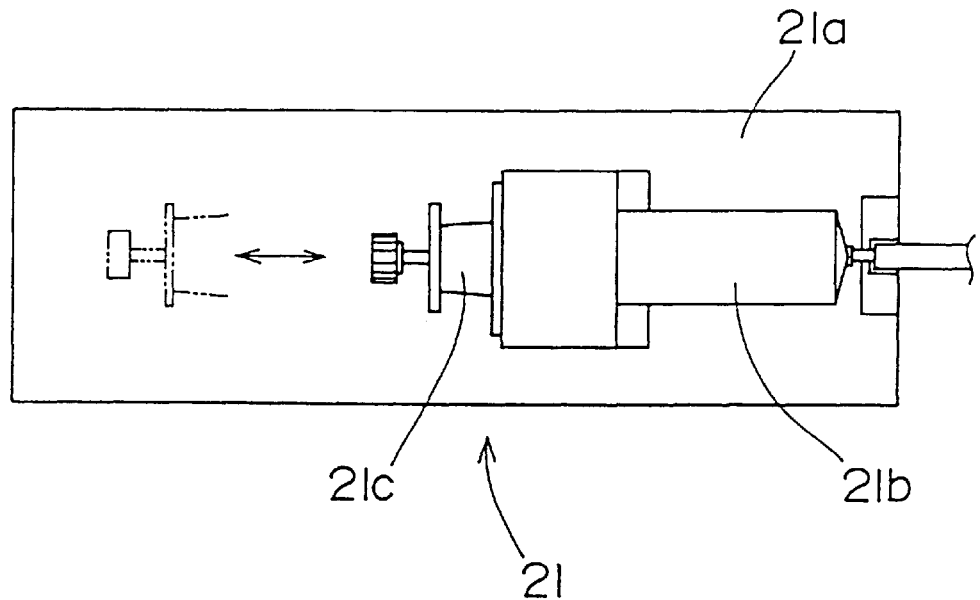
F I G. 10B
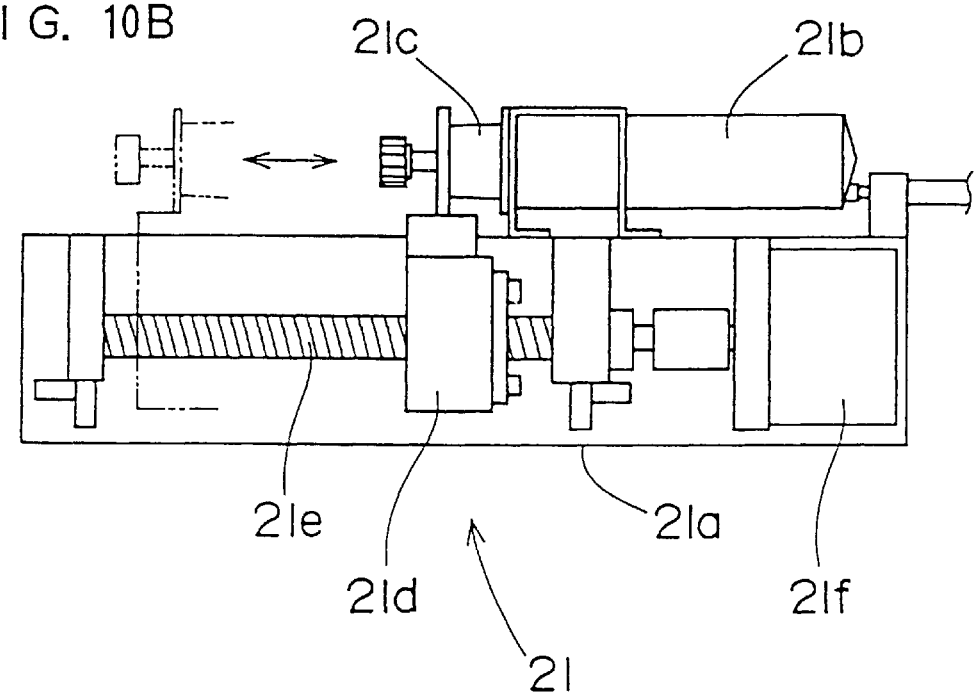

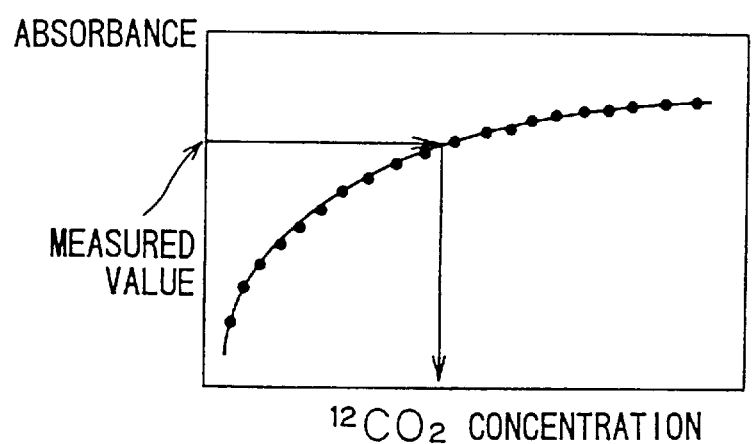
F I G. 17A
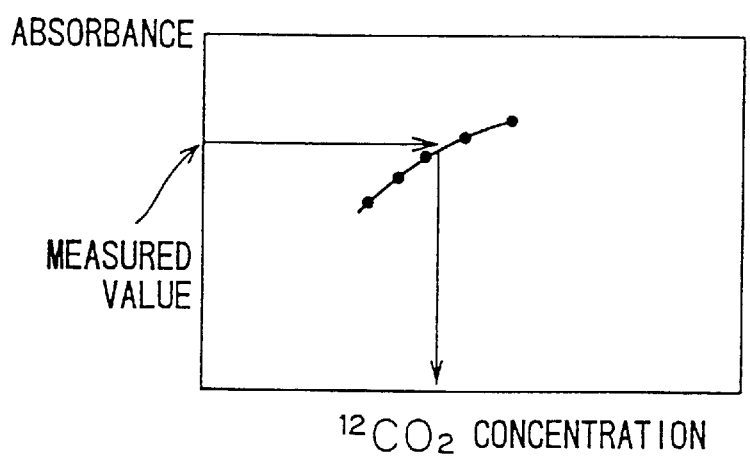
F I G. 17B

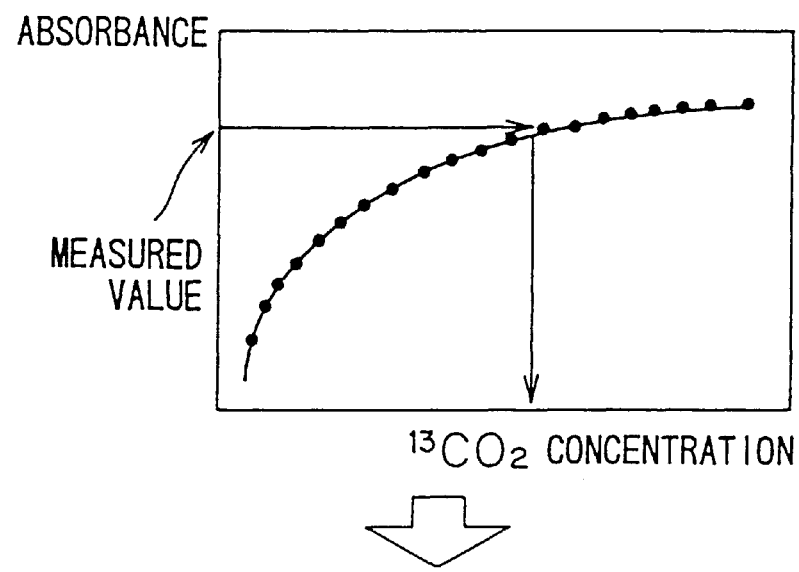
F I G. 18A
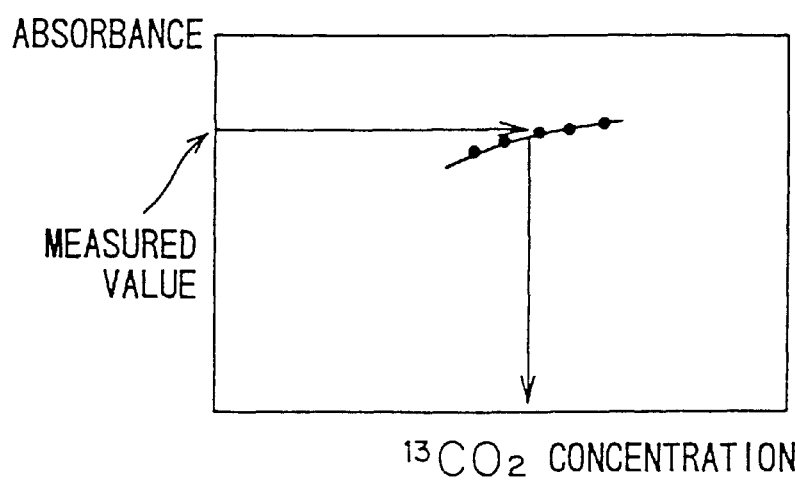
F I G. 18B

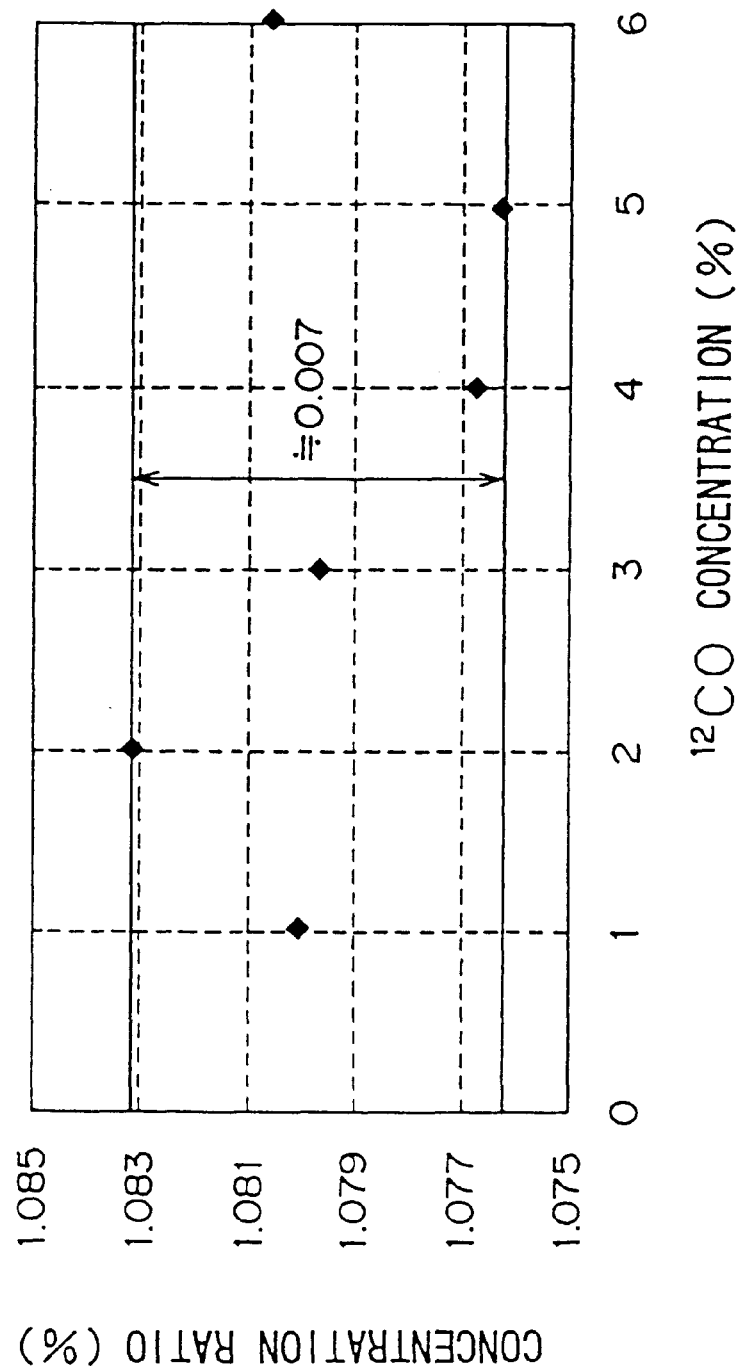
F I G. 20

F I G. 22
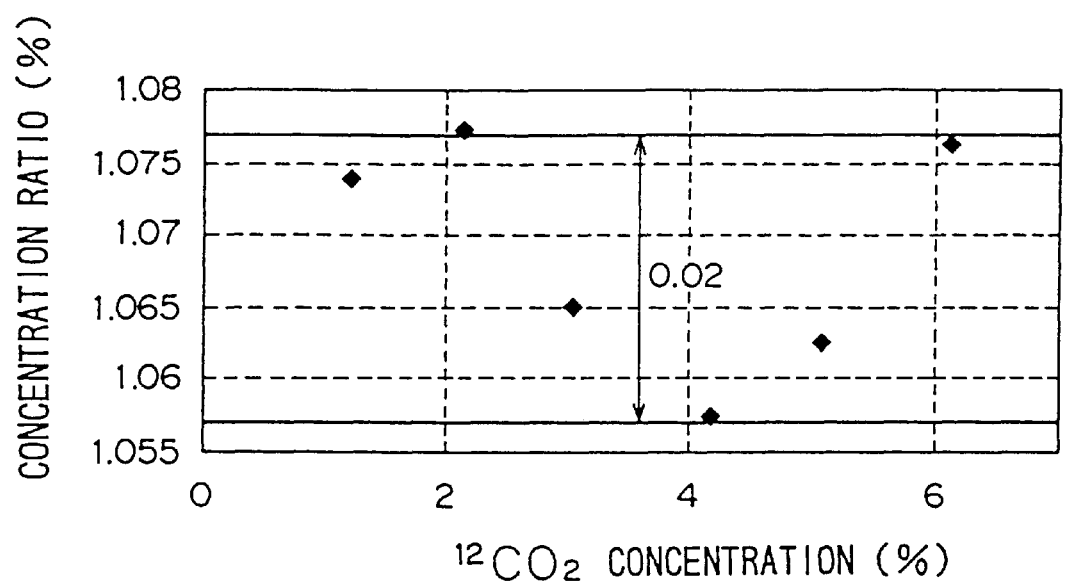

F I G. 23
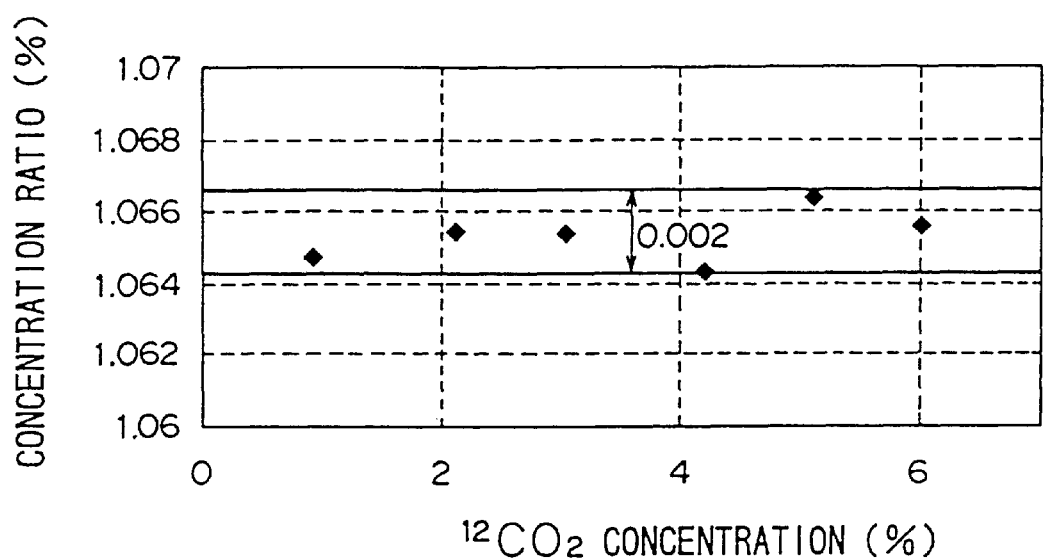

METHOD FOR SPECTROMETRICALLY MEASURING ISOTOPIC GAS AND APPARATUS THEREOF

This application is a division of Ser. No. 08/849,351, filed Jun. 6, 1997, which is a 371 of PCT/JP96/02876, filed Oct. 2, 1996.

TECHNICAL FIELD

The present invention relates to methods and apparatuses for spectrometrically measuring the concentration of an isotopic gas on the basis of a difference in the light absorption characteristics of the isotope.

BACKGROUND ART

Isotopic analyses are useful for diagnosis of a disease in a medical application, in which metabolic functions of a living body can be determined by measuring a change in the concentration or concentration ratio of an isotope after administration of a drug containing the isotope. In the other fields, the isotopic analyses are used for studies of the photosynthesis and metabolism of plants, and for ecological tracing in a geochemical application.

It is generally known that gastric ulcer and gastritis are caused by bacteria called helicobacter pylori (HP) as well as by a stress. If the HP is present in the stomach of a patient, an antibiotic or the like should be administered to the patient for bacteria removal treatment. Therefore, it is indispensable to check if the patient has the HP. The HP has a strong urease activity for decomposing urea into carbon dioxide and ammonia.

Carbon has isotopes having mass numbers of 12, 13 and 14, among which $^{13}C$ having a mass number of 13 is easy to handle because of its non-radioactivity and stability.

If the concentration of $^{13}CO_2$ (a final metabolic product) or the concentration ratio of $^{13}CO_2$ to $^{12}CO_2$ in breath of a patient is successfully measured after urea labeled with the isotope $^{13}C$ is administered to the patient, the presence of the HP can be confirmed.

However, the concentration ratio of $^{13}CO_2$ to $^{12}CO_2$ in naturally occurring carbon dioxide is 1:100. Therefore, it is difficult to determine the concentration ratio in the breath of the patient with high accuracy.

There have been known methods for determining the concentration ratio of $^{13}CO_2$ to $^{12}CO_2$ by means of infrared spectroscopy (see JPB 61(1986)-42219 and JPB 61(1986)-42220).

In the method disclosed in JPB 61(1986)-42220, two cells respectively having a long path and a short path are provided, the path lengths of which are adjusted such that the light absorption by $^{13}CO_2$ in one cell is equal to the light absorption by $^{12}CO_2$ in the other cell. Light beams transmitted through the two cells are lead to spectrometric means, in which the light intensities are measured at wavelengths each providing the maximum sensitivity. In accordance with this method, the light absorption ratio can be adjusted to "1" for the concentration ratio of $^{13}CO_2$ to $^{12}CO_2$ in naturally occurring carbon dioxide. If the concentration ratio is changed, the light absorption ratio also changes by the amount of a change in the concentration ratio. Thus, the change in the concentration ratio can be determined by measuring a change in the light absorption ratio.

(A) However, the method for determining the concentration ratio according to the aforesaid document suffers from the following drawbacks.

Calibration curves for determining the concentrations of $^{12}CO_2$ should be prepared by using gaseous samples each having a known $^{12}CO_2$ concentration.

To prepare the calibration curve for the $^{12}CO_2$ concentration, the $^{12}CO_2$ absorbances are measured for different $^{12}CO_2$ concentrations. The $^{12}CO_2$ concentrations and the $^{12}CO_2$ absorbances are plotted as abscissa and ordinate, respectively, and the calibration curve is determined by the method of least squares.

The calibration curve for the $^{13}CO_2$ concentration is prepared in the same manner as described above.

For determination of the concentrations by means of infrared spectroscopy, the preparation of the calibration curves is based on an assumption that the relation between the concentration and the absorbance conforms to the Lambert-Beer Law. However, the Lambert-Beer Law itself is an approximate expression. The actual relation between the concentration and the absorbance does not always conform to the Lambert-Beer Law. Therefore, all the plotted data do not perfectly fit to the calibration curve.

FIG. 1 is a graphical representation in which concentration ratios of $^{13}CO_2$ to $^{12}CO_2$ are plotted with respect to $^{12}CO_2$ concentrations, the $^{12}CO_2$ concentrations and the $^{13}CO_2$ concentrations having been determined by using calibration curves prepared on the basis of measurements of the absorbances of gaseous samples having the same concentration ratio ($^{13}CO_2$ concentration/$^{12}CO_2$ concentration= 1.077%) but different $^{12}CO_2$ concentrations.

As shown in FIG. 1, the concentration ratios determined for different $^{12}CO_2$ concentrations deviate from the actual concentration ratio (1.077%), and form an undulatory curve when plotted.

Although the cause of the deviation has not been elucidated yet, the deviation supposedly results from changes in the spectroscopic characteristics such as reflectance, refractive index and stray light in dependence on the $^{12}CO_2$ concentration and from the error characteristics of the least square method employed for the preparation of the calibration curves.

If the concentration of a component gas is determined without correction of the characteristics associated with the deviation, a critical error may result.

(B) A variety of experiments have revealed that, where the infrared spectrometry is employed to measure the concentration of $^{13}CO_2$ or the concentration ratio of $^{13}CO_2$ to $^{12}CO_2$ (hereinafter referred to as "$^{13}CO_2$ concentration ratio"), measurement results differ from the actual $^{13}CO_2$ concentration or $^{13}CO_2$ concentration ratio depending on the concentration of oxygen contained in a gaseous sample.

FIG. 2 is a graphical representation in which $^{13}CO_2$ concentration ratios are plotted with respect to oxygen contents, the $^{13}CO_2$ concentration ratios having been determined by measuring gaseous samples containing $^{13}CO_2$ diluted with oxygen and nitrogen and having the same $^{13}CO_2$ concentration but different oxygen concentrations. The determined $^{13}CO_2$ concentration ratios are normalized on the basis of a $^{13}CO_2$ concentration ratio for an oxygen content of 0%.

As shown in FIG. 2, the $^{13}CO_2$ concentration ratio is not constant but varies depending on the oxygen concentration.

If the $^{13}CO_2$ concentration or the $^{13}CO_2$ concentration ratio of a gaseous sample containing oxygen is measured in ignorance of this fact, it is obvious that a measurement differs from an actual value.

FIG. 3 is a graphical representation illustrating the result of measurement in which gaseous samples having different $^{13}CO_2$ concentration ratios and containing no oxygen were measured. In FIG. 3, the actual $^{13}CO_2$ concentration ratios and the measured $^{13}CO_2$ concentration ratios are plotted as abscissa and ordinate, respectively. The $^{13}CO_2$ concentration ratios are normalized on the basis of the minimum $^{13}CO_2$ concentration ratio.

FIG. 4 is a graphical representation illustrating the result of measurement in which gaseous samples having different $^{13}CO_2$ concentration ratios and containing various concentration of oxygen (up to 90%) were measured. In FIG. 4, the actual $^{13}CO_2$ concentration ratios and the measured $^{13}CO_2$ concentration ratios are plotted as abscissa and ordinate, respectively. The $^{13}CO_2$ concentration ratios are normalized on the basis of the minimum $^{13}CO_2$ concentration ratio.

A comparison between the results shown in FIGS. 3 and 4 indicates that the relationship between the actual $^{13}CO_2$ concentration ratio and the measured $^{13}CO_2$ concentration ratio in FIG. 3 is about 1:1 (or the scope of the fitting curve in FIG. 3 is about 1) while the relationship between the actual $^{13}CO_2$ concentration ratio and the measured $^{13}CO_2$ concentration ratio in FIG. 4 is about 1:0.3 (or the scope of the linear fitting curve in FIG. 4 is about 0.3).

Thus, the measurement of the $^{13}CO_2$ concentration or the $^{13}CO_2$ concentration ratio is influenced by the concentration of oxygen contained in a gaseous sample, the cause of which has not been elucidated yet.

If the concentration or concentration ratio of a component gas is determined without performing a correction in consideration of the oxygen concentration, it is predicted that a critical error may result.

(C) Since the concentration of $CO_2$, particularly, the concentration of $^{13}CO_2$ is extremely low, highly sensitive measurement is required. When the sensitivity of measurement is increased, a measured light intensity is responsive to changes in parameters of the measurement system, e.g., the light intensity of a light source, the temperature of a sample gas, the temperature of a cell to which the gas is introduced, the sensitivity of a photodetector and the like. Thus, the measured value may have an error caused by factors not related to the sample gas.

To solve this problem, the measurement is started after the measurement system is stabilized in a time-consuming manner. This reduces the operation efficiency and makes it impossible to meet a user demand to measure a large amount of samples in a short time.

For measurement of one breath sample, the $^{12}CO_2$ absorbance is measured and the $^{12}CO_2$ concentration is determined on the basis of a calibration curve for $^{12}CO_2$. The $^{13}CO_2$ absorbance is measured and the $^{13}CO_2$ concentration is calculated on the basis of a calibration curve for $^{13}CO_2$, as well. The measurement of another breath sample is carried out in the same manner.

If the $CO_2$ concentrations of the aforesaid two breath samples are at substantially the same level, the ranges of the calibration curves for $^{12}CO_2$ and $^{13}CO_2$ to be used for the concentration determination can be limited. Thus, the measurement accuracy can be increased by using limited ranges of the calibration curves.

(D) In a conventional infrared spectrometric method as described above, a bag containing a gaseous sample is connected to a predetermined pipe of a spectrometric apparatus, and the gaseous sample is introduced into a cell through the pipe by manually compressing the bag.

However, even small turbulence may drastically reduce the measurement accuracy because the absorbance of $^{13}CO_2$ present in a trace amount is measured in the isotopic gas analysis. The gaseous sample cannot be passed through the cell at a constant flow rate by the manual compression of the bag. This generates a nonuniform flow of the gaseous sample in the cell and causes the gaseous sample to have a local temperature change and an incidental concentration change, thereby fluctuating a light detection signal.

The flow rate of the gaseous sample may be controlled to be constant by using a pump and a flow meter in combination. However, the accuracy of the flow control cannot be ensured, because the volume of the bag containing the gaseous sample is small and the flow rate is low. Alternatively, an apparatus called mass flow meter for electronic flow control may be employed as flow control means. This improves the accuracy of the flow rate control, but results in a complicated apparatus and an increased cost.

(E) In the method disclosed in JPB 61(1986)-42220, the length of the cell is reduced and, therefore, a cell-absent space is filled with air. The air space hinders highly accurate measurement. If the lengths of paths between the light source and the cell and between the cell and the photoreceptor are increased, highly accurate measurement may be hindered.

More specifically, since the absorbance of $^{13}CO_2$ present in a trace amount is measured in the isotopic gas measurement, even a small external disturbance reduces the measurement accuracy. A few percentage of $^{12}CO_2$ and a trace amount of $^{13}CO_2$ are present in the aforesaid air space and spaces between the light source and the cell and between the cell and the photoreceptor. A $^{13}CO_2$ spectrum partially overlaps a $^{12}CO_2$ spectrum and, if a filter is used, the band-pass width thereof influences the measurement. Therefore, the presence of $^{12}CO_2$ indirectly influences the measurement of the $^{13}CO_2$ absorbance, and the trace amount of $^{13}CO_2$ directly influences the measurement of the $^{13}CO_2$ absorbance.

To eliminate the influence of $CO_2$ present in a light path, an apparatus (see JPB 3(1991)-31218) has been proposed in which a light source, a sample cell, a reference cell, a interference filter, a detection element and like elements are accommodated in a sealed case which is connected to a column filled with a $CO_2$ absorbent through a tube and a circulation pump for circulating air within the sealed case and the column to remove $CO_2$ from the air in the sealed case.

The apparatus disclosed in this document can remove $CO_2$ which may adversely affect the measurement, but requires the column filled with the $CO_2$ absorbent, the tube and a large sealed case for accommodating the respective elements, resulting in a large-scale construction. In addition, the fabrication of the apparatus requires a laborious process such as for sealing the large case.

Further, a nonuniform flow of the air within the sealed case causes a local temperature change and an incidental concentration change, thereby causing a light detection signal to be fluctuated.

(F) In the infrared spectroscopic measurement, breath is sampled in breath sampling bags before and after a diagnostic drug is administered to a living body, and the breath samples in the breath sampling bags are respectively measured for determination of the $^{13}CO_2$ concentration or the $^{13}CO_2$ concentration ratio.

The measurement of such breath samples is typically performed in a professional manner in a measurement organization, which manipulates a large amount of samples in a short time. Therefore, breath samples obtained before and after the drug administration are often mistakenly manipulated.

More specifically, breath samples obtained from one patient before and after the drug administration are mistaken for those obtained from another patient, or a breath sample obtained before the drug administration is mistaken for that obtained after the drug administration.

Such mistakes lead to erroneous measurement results and, therefore, should be assuredly prevented.

Further, if a breath sample includes a gas remaining in the oral cavity of a patient, the measurement accuracy is reduced. To reduce a measurement error, breath from the lung of the patient should be sampled.

Still further, since moisture in a breath sample adversely affects the optical measurement, the moisture should be removed from the breath sample. Furthermore, a consideration should be given to the breath sampling bag to prevent the breath sample from escaping from the bag.

It is an object of the present invention to provide a method for spectrometrically measuring an isotopic gas, which is employed to precisely determine the concentration or concentration ratio of a component gas in a gaseous test sample containing a plurality of component gases by way of spectrometry when the gaseous test sample is introduced into a cell.

It is another object of the present invention to provide a method for spectrometrically measuring an isotopic gas, which is employed to precisely determine the concentration of a component gas in a gaseous test sample containing a plurality of component gases by way of spectrometry by using a limited range of a calibration curve when the gaseous test sample is introduced into a cell.

It is further another object of the present invention to provide a method for spectrometrically measuring an isotopic gas, which is employed to precisely determine the concentration or concentration ratio of $^{13}CO_2$ contained in a gaseous test sample by way of spectrometry in consideration of the concentration of oxygen when the gaseous test sample into a cell.

It is still another object of the present invention to provide a method for spectrometrically measuring an isotopic gas, which is employed to precisely determine the concentration or concentration ratio of a component gas in a gaseous test sample containing a plurality of component gases by way of spectrometry in such a manner that time-related influences on a measurement system can be minimized when the gaseous test sample is introduced into a cell.

It is yet another object of the present invention to provide an apparatus for spectrometrically measuring an isotopic gas, which has a simple construction and is capable of introducing a gaseous test sample containing a plurality of component gases at a constant flow rate for spectrometry.

It is still another object of the present invention to provide a breath sampling bag, which is given a consideration to assuredly prevent a breath sample from being mistakenly manipulated.

It is yet another object of the present invention to provide a breath sampling bag, which prevents the sampling of air present in the oral cavity of a patient but allows the sampling of breath from the lung of the patient.

It is still another object of the present invention to provide a breath sampling bag, which is capable of removing moisture from breath blown therein.

It is yet another object of the present invention to provide a breath sampling bag, which has a construction to prevent a breath sample from being escaped therefrom.

SUMMARY OF THE INVENTION

To achieve the aforesaid objects, the present invention provides a method for spectrometrically measuring an isotopic gas comprising the steps of introducing a gaseous test sample containing a plurality of component gases into a cell, measuring intensity of light transmitted through the gaseous test sample at wavelengths suitable for the respective component gases, and processing data of the light intensity to determine concentrations of the component gases in the gaseous test sample, the method characterized by: a first step of introducing the gaseous test sample into the cell and measuring absorbances of the respective component gases in the gaseous test sample; a second step of determining concentrations and concentration ratios of the component gases in the gaseous test sample on the basis of calibration curves; and a third step of obtaining concentration ratio correction values for the component gases on the basis of the concentrations of the component gases obtained in the second step by using correction cures preliminary prepared by measuring absorbances of the component gases in gaseous samples containing the respective component gases in known concentrations with known concentration ratios, determining concentrations and concentration ratios of the component gases in the gaseous samples on the basis of the calibration curves, and by plotting the thus determined concentrations and concentration ratios of the component gases in the gaseous samples, and respectively dividing the concentration ratios of the component gases obtained in the second step by the concentration ratio correction values for the component gases, thereby correcting the concentration ratios of the component gases in the gaseous test sample.

In comparison with the prior-art method, the aforesaid method includes an additional step (the third step) of correcting the concentration ratio of a component gas in a gaseous test sample on the basis of the concentration of the component gas by using a correction curve prepared by measuring gaseous samples respectively containing the component gas in known concentrations or known concentration ratios. The correction of the concentration ratio eliminates the conventionally experienced drawback that the measured concentration ratios of the component gas which should basically be the same vary depending on the concentration of the component gas, thereby improving the measurement accuracy of the concentration ratio of the component gas.

Another method for spectrometrically measuring an isotopic gas in accordance with the present invention comprises the steps of introducing a gaseous test sample containing a plurality of component gases into a cell, measuring intensity of light transmitted through the gaseous test sample at wavelengths suitable for the respective component gases, and processing data of the light intensity to determine concentrations of the component gases in the gaseous test sample, the method characterized by: a first step of introducing the gaseous test sample into the cell and measuring absorbances of the respective component gases in the gaseous test sample; a second step of tentatively determining concentrations of the component gases in the gaseous test sample on the basis of calibration curves prepared by using data obtained by measuring gaseous samples respectively containing the component gases in known concentrations within a predetermined range; and a third step of preparing new calibration curves by using some of the data within limited ranges around the concentrations of the component gases in the gaseous test sample tentatively determined in the second step, and determining concentrations of the component gases in the gaseous test sample by using the calibration curves thus prepared.

In this method, the concentration of a component gas is tentatively determined with the use of a calibration curve which is prepared on the basis of data obtained by measuring gaseous samples containing the component gas in known concentrations within a predetermined range (the second step). However, all the data do not perfectly fit to the calibration curve on which the tentatively determined concentration of the component gas is based, as described in "Background Art".

For this reason, another calibration curve is prepared by using some of the data within a limited range around the concentration of the component gas determined in the second step. It is confirmed that part of the calibration curve prepared on the basis of the data in the narrower range strictly conforms to the Lambert-Beer Law. Therefore, the concentration of the component gas is determined on the basis of the absorbance thereof by using the calibration curve thus prepared (the third step).

Since the accuracy of the calibration curve is improved over the prior art method, the obtained concentration of the component gas is more accurate. Thus, the measurement accuracy of the concentration of the component gas can be increased.

Further another method for spectrometrically measuring an isotopic gas in accordance with the present invention comprises the steps of introducing a gaseous test sample containing $^{13}CO_2$ into a cell, measuring an intensity of light transmitted through the gaseous test sample at a wavelength suitable for $^{13}CO_2$, and processing data of the light intensity to determine a concentration of $^{13}CO_2$ in the gaseous test sample, the method characterized by: a first step of introducing the gaseous test sample into the cell and measuring an absorbance of $^{13}CO_2$ in the gaseous test sample; a second step of determining a concentration of $^{13}CO_2$ in the gaseous test sample on the basis of a calibration curve; and a third step of measuring an oxygen concentration in the gaseous test sample, obtaining a concentration correction value for $^{13}CO_2$ on the basis of a correction curve and the measured oxygen concentration, said correction curve being preliminary prepared by measuring absorbances of $^{13}CO_2$ in gaseous samples containing $^{13}CO_2$ and oxygen in known concentrations, determining concentrations of $^{13}CO_2$ in the gaseous samples on the basis of the calibration curve, and by plotting the concentrations of $^{13}CO_2$ thus determined with respect to the oxygen concentrations, and dividing the concentration of $^{13}CO_2$ obtained in the second step by the concentration correction value for $^{13}CO_2$ determined on the basis of the correction curve, thereby correcting the concentration of $^{13}CO_2$ in the gaseous test sample.

A further method for spectrometrically measuring an isotopic gas, comprises the steps of introducing a gaseous test sample containing $^{12}CO_2$ and $^{13}CO_2$ into a cell, measuring intensity of light transmitted through the gaseous test sample at wavelengths suitable for $^{12}CO_2$ and $^{13}CO_2$, and processing data of the light intensity to determine concentrations of or a concentration ratio between $^{13}CO_2$ and $^{12}CO_2$ in the gaseous test sample, the method characterized by: a first step of introducing the gaseous test sample into the cell and measuring absorbances of $^{12}CO_2$ and $^{13}CO_2$ in the gaseous test sample; a second step of determining concentrations of or a concentration ratio between $^{13}CO_2$ and $^{12}CO_2$ in the gaseous test sample on the basis of calibration curves; and a third step of measuring an oxygen concentration in the gaseous test sample, obtaining concentration correction values or a concentration ratio correction value for $^{13}CO_2$ and $^{12}CO_2$ on the basis of correction curves and the measured oxygen concentration, said correction curves being preliminary prepared by measuring absorbances of $^{12}CO_2$ and $^{13}CO_2$ in gaseous samples containing $^{12}CO_2$, $^{13}CO_2$ and oxygen in known concentrations, determining concentrations of or concentration ratios between $^{13}CO_2$ and $^{12}CO_2$ in the gaseous samples on the basis of the calibration curves, and by plotting the concentrations of or the concentration ratios between $^{13}CO_2$ and $^{12}CO_2$ thus determined with respect to the oxygen concentrations, and respectively dividing the concentrations of or the concentration ratio between $^{13}CO_2$ and $^{12}CO_2$ determined in the second step by the concentration correction values or the concentration ratio correction value determined on the basis of the correction curves, thereby correcting the concentrations of or the concentration ratio between $^{13}CO_2$ and $^{12}CO_2$ in the gaseous test sample.

In comparison with the prior art method, the aforesaid method includes an additional step (the third step) of correcting the concentration or concentration ratio of a component gas in a gaseous test sample on the basis of a measured oxygen concentration of the gaseous test sample by using a correction curve prepared by measuring gaseous samples respectively containing oxygen in known concentrations.

The correction eliminates the newly encountered drawback that the measured concentrations of the component gas which should basically be the same vary depending on the oxygen concentration, thereby improving the measurement accuracy of the concentration or concentration ratio of the component gas.

The oxygen concentration may be determined by means of any of various oxygen sensors or by spectrometrically measuring an absorbance in an oxygen molecular spectrum.

Still another method for spectrometrically measuring an isotopic gas in accordance with the present invention comprises the steps of introducing a gaseous test sample containing a plurality of component gases into a cell, measuring absorbances of light transmitted through the gaseous test sample at wavelengths suitable for the respective component gases, and determining concentrations of the respective component gases on the basis of calibration curves prepared by measuring gaseous samples respectively containing the component gases in known concentrations, the method characterized in that a reference gas measurement in which a light intensity is measured with a reference gas filled in the cell and a sample measurement in which a light intensity is measured with the gaseous test sample filled in the cell are alternately performed; and the absorbances are determined on the basis of the light intensity obtained in the sample measurement and an average of light intensity obtained in the reference gas measurements performed before and after the sample measurement.

It is a conventional practice that a reference gas measurement in which a light intensity is measured with a reference gas filled in a cell and a sample measurement in which a light intensity is measured with a gaseous sample filled in the cell are each performed once for measurement of an absorbance. In the aforesaid method, however, the absorbance is determined on the basis of the light intensity measured in the sample measurement and an average of light intensity measured in the reference gas measurements performed before and after the sample measurement.

Therefore, a time-related variation of the absorbances measured before and after the sample measurement can be corrected by using the average of the light intensity obtained in the reference gas measurement. Thus, an influence of the time-related change of the measurement system can be eliminated.

The result of the reference gas measurement performed after the sample measurement can serve as the result of the reference gas measurement performed before the next sample measurement. Therefore, one measurement result for the reference gas can be used twice.

Yet another method for spectrometrically measuring an isotopic gas in accordance with the present invention comprises the steps of introducing a gaseous test sample containing a plurality of component gases into a cell, measuring absorbances of light transmitted through the gaseous test sample at wavelengths suitable for the respective component gases and determining concentrations of the respective component gases on the basis of calibration curves prepared by measuring gaseous samples respectively containing the component gases in known concentrations, the method characterized in that a reference gas measurement in which a light intensity is measured with a reference gas filled in the cell and a sample measurement in which a light intensity is measured with the gaseous test sample filled in the cell are alternately performed, and the absorbances are determined on the basis of the light intensity obtained in the reference gas measurement and an average of light intensity obtained in the sample measurements performed before and after the reference gas measurement.

In this method, an absorbance is determined on the basis of a light intensity measured in a reference gas measurement and an average of light intensity measured in sample measurements performed before and after the reference gas measurement.

Since the measurement should be performed twice on the same gaseous sample, the operation efficiency is reduced. However, a time-related variation of the absorbances obtained before and after the sample measurement can be corrected by using the average of the light intensity obtained in the sample measurement. Thus, an influence of the time-related change of the measurement system can be eliminated.

Still another method for spectrometrically measuring an isotopic gas in accordance with the present invention comprises the steps of introducing a gaseous test sample containing $^{12}CO_2$ and $^{13}CO_2$ as component gases into a cell, measuring absorbances of light transmitted through the gaseous test sample at wavelengths suitable for the respective component gases, and determining concentrations of the respective component gases on the basis of calibration curves prepared by measuring gaseous samples respectively containing the component gases in known concentrations, the method characterized in that two gaseous test samples obtained from one body are measured and, if a concentration of $^{12}CO_2$ in one of the two gaseous test samples is higher than a concentration of $^{12}CO_2$ in the other gaseous test sample, said one gaseous test sample is diluted to a $^{12}CO_2$ concentration level equivalent to that of the other gaseous test sample, and then $^{13}CO_2/^{12}CO_2$ concentration ratios in the respective gaseous test samples are determined.

In this method, two breath test samples can be measured on condition that the $CO_2$ concentrations thereof are at the same level and, therefore, a range of a calibration curve to be used can be limited. The accuracy of the measurement can be improved as the range of the calibration curve to be used becomes narrower. Hence, the measurement accuracy can be improved by using a limited range of the calibration curve.

Yet another method for spectrometrically measuring an isotopic gas in accordance with the present invention comprises the above method, further characterized by a preliminary measurement and a main measurement, wherein concentrations of $CO_2$ in first and second gaseous test samples obtained from one body are respectively measured in the preliminary measurement and, if the measured concentration of $CO_2$ in the first gaseous test sample is higher than the measured concentration of $CO_2$ in the second gaseous test sample, the first gaseous test sample is diluted to a $CO_2$ concentration level equivalent to that of the second gaseous test sample, then a $^{13}CO_2/^{12}CO_2$ concentration ratio in the first gaseous test sample thus diluted is determined and a $^{13}CO_2/^{12}CO_2$ concentration ratio in the second gaseous test sample is determined in the main measurement or if the measured concentration of $CO_2$ in the first gaseous test sample is lower than the measured concentration of $CO_2$ in the second gaseous test sample, a $^{13}CO_2/^{12}CO_2$ concentration ratio in the first gaseous test sample is determined, then the second gaseous test sample is diluted to a $CO_2$ concentration level equivalent to that of the first gaseous test sample, and a $^{13}CO_2/^{12}CO_2$ concentration ratio in the second gaseous test sample thus diluted is determined in the main measurement. This method is based on a premise that a first gaseous sample is filled in a cell for light intensity measurement thereof and, after the first gaseous sample is discharged from the cell, a second gaseous sample is filled in the same cell for light intensity measurement thereof.

To achieve the aforesaid objects, the present invention provides an apparatus for spectrometrically measuring an isotopic gas, which includes a gas injection means for sucking therein a gaseous sample and then injecting the gaseous sample into a cell by mechanically pushing out the gaseous sample at a constant flow rate.

With this construction, the gaseous sample is injected into the cell at a constant flow rate. Therefore, the gaseous sample uniformly flows within the cell, so that a highly accurate light detection signal free from fluctuation can be provided for more accurate concentration measurement.

Usable as the gas injection means for mechanically pushing out the gaseous sample at the constant rate is, for example, a mechanism including a piston and a cylinder and adapted to move the cylinder at a constant rate.

In accordance with another aspect of the present invention, the apparatus for spectrometrically measuring an isotopic gas further includes a temperature maintaining means for maintaining a cell for receiving the gaseous sample introduced therein at a constant temperature.

By keeping the temperature within the cell constant, the temperature condition of the gaseous sample can be kept uniform, so that a highly accurate light detection signal free from fluctuation can be provided.

To achieve the aforesaid objects, the present invention provides another apparatus for spectrometrically measuring an isotopic gas, which includes a cell for receiving a gaseous sample introduced therein positioned in the midst of a light path between a light source and a photoreceptor, and a reference cell disposed in a portion of the light path not occupied by the cell and filled with a reference gas having no absorption at a wavelength for measurement.

Where a measuring vessel is not provided with the reference cell and filled with air which contains component gases of the same kinds as contained in the gaseous sample, an adverse effect is caused due to the component gases present in the measuring vessel. With the aforesaid construction, however, the reference cell filled with the reference gas having no absorption at the measurement wavelength is disposed in the light path, thereby eliminating the optically adverse effect. Thus, the concentration measurement can be performed more accurately.

Further another apparatus for spectrometrically measuring an isotopic gas in accordance with the present invention includes two cells each disposed parallel to a light path between a light source and a photoreceptor and having different lengths for receiving a gaseous sample introduced therein, and a reference cell disposed between a shorter one of the two cells and the photoreceptor or between the shorter cell and the light source and filled with a reference gas having no absorption at a wavelength for measurement.

With the cells having different lengths, a large space is present between the shorter cell and the photoreceptor or between the light source and the shorter cell, and component gases of the same kinds as contained in the gaseous sample are present in the space and adversely affect the optical measurement. More accurate concentration measurement can be ensured by providing in the space the reference cell filled with the reference gas having no absorption at the measurement wavelength.

In accordance with further another aspect of the present invention, the aforesaid apparatuses for spectrometrically measuring an isotopic gas each further include a gas flow generating means for constantly passing the reference gas through the reference cell at a constant flow rate.

The passing of the reference gas through the reference cell is based on the following consideration. If the reference cell is sealed with the reference gas filled therein, the reference gas gradually leaks from a joint of the cell and is replaced with outside air. The air which has entered the cell contains component gases of the same kinds as contained in the gaseous sample, resulting in an optically adverse effect. Further, the reference gas constantly flowing at a constant rate does not generate a nonuniform gas flow within the reference cell, thereby preventing a light detection signal from being fluctuated.

The gas flow generating means may comprise a valve for introducing the reference gas from a gas container, a pipe and a flow meter, for example.

In accordance with yet another aspect of the present invention, the aforesaid apparatus for spectrometrically measuring an isotopic gas further includes a temperature maintaining means for maintaining the cell for receiving the gaseous sample introduced therein and the reference cell at a constant temperature.

By keeping the temperature within the cell and the reference cell constant, a temperature difference between the gaseous sample and the reference gas can be eliminated, so that the thermal conditions of the gaseous sample and the reference gas can be kept equivalent. Thus, the absorbances can be determined accurately.

To achieve the aforesaid objects, the present invention provides a breath sampling bag, which includes a plurality of breath accumulating chambers joined together for respectively accumulating a plurality of breath samples, and a plurality of breath introduction pipes for respectively introducing the breath samples from the plurality of breath accumulating chambers into a plurality of inlets of a gas measuring apparatus for measuring a breath sample, the plurality of breath introduction pipes each being configured such as to be prevented from being connected to the inlets of the gas measuring apparatus in a wrong way.

A gas measuring apparatus in accordance with the present invention is adapted to measure breath samples contained in a breath sampling bag which includes a plurality of breath accumulating chambers joined together and a plurality of breath introduction pipes for introducing therethrough a plurality of breath samples from a living body into the respective breath accumulating chambers, and includes a plurality of breath inlets for respectively introducing the breath samples from the breath accumulating chambers through the breath introduction pipes, the plurality of breath inlets each being configured such as to prevent the breath introduction pipes from being connected thereto in a wrong way.

With the breath sampling bag and gas measuring apparatus of the aforesaid constructions, such an inconvenient accident can be eliminated that one breath sample in one breath accumulating chamber of the breath sampling bag is introduced into the gas measuring apparatus mistakenly for another breath sample in another breath accumulating chamber.

Where breath is sampled from a living body before and after a diagnostic drug is administered to the living body and the $^{13}CO_2$ concentration or $^{13}CO_2$ concentration ratio of the breath samples is measured, for example, the manipulation mistake of the breath samples obtained before and after the administration of the diagnostic drug for measurement can be prevented. Further, where a load test is performed and breath is sampled at a predetermined time interval after the administration of a diagnostic drug, breath samples thus obtained are prevented from being measured in a wrong order.

The breath introduction pipes or the breath inlets are, for example, asymmetrically configured for prevention of the connection mistake of the breath sampling bag. For asymmetrical configuration, the plurality of breath introduction pipes may have different diameters, lengths and cross-sections, and the plurality of breath inlets may have different diameters, lengths and cross-sections corresponding to those of the respective breath introduction pipes.

Another breath sampling bag in accordance with the present invention includes a breath accumulating chamber for accumulating breath and a breath introduction pipe for introducing the breath from a living body into the breath accumulating chamber, the breath introduction pipe having a resistance generating means for generating a resistance to the blowing of the breath during the sampling of the breath.

With this construction, the provision of the resistance generating means prevents the sampling of breath present in the oral cavity of the living body, but enables the sampling of breath from the lung thereof. Thus, a measurement error can be reduced.

The resistance generating means is embodied by allowing the interior of the breath introduction pipe to have some change which generates a resistance to the blowing of the breath. For example, the inner diameter of the breath introduction pipe may be reduced or, alternatively, a resistance component may be provided on the interior of the breath introduction pipe.

Further another breath sampling bag in accordance with the present invention includes a breath accumulating chamber for accumulating breath and a breath introduction pipe for introducing the breath from a living body into the breath accumulating chamber, the breath introduction pipe having a detachable filter for removing moisture from the breath during the sampling of the breath.

With this construction, the moisture in the breath can be removed therefrom by means of the filter, so that a reduction in the optical measurement accuracy can be prevented. The removal of moisture is particularly effective for infrared spectrometry.

Still another breath sampling bag in accordance with the present invention includes a breath accumulating chamber for accumulating breath and a breath introduction pipe for introducing the breath from a living body into the breath accumulating chamber, the breath introduction pipe having a valve for preventing the back flow of the breath during the sampling of the breath.

With this construction, the provision of the back-flow prevention valve in the breath introduction pipe prevents the breath from leaking out of the breath sampling bag.

Another gas measuring apparatus in accordance with the present invention, which is adapted to measure a breath sample contained in a breath sampling bag including a breath accumulating chamber for accumulating the breath sample and a breath introduction pipe with a back-flow prevention valve for introducing the breath sample from a living body into the breath accumulating chamber, includes a breath inlet for introducing therein the breath sample from the breath sampling bag through the breath introduction pipe, the breath inlet having means for disabling the function of the valve with the breath introduction pipe being connected to the breath inlet.

With this construction, the function of the valve can be disabled with the breath introduction pipe being connected to the breath inlet when the breath sample is to be introduced into the gas measuring apparatus through the breath introduction pipe. Therefore, the breath sample can be smoothly introduced into the gas measuring apparatus.

The means for disabling the function of the valve is embodied, for example, by providing a long pin projecting from the breath inlet, which is adapted to forcibly open the valve when the breath introduction pipe is connected to the breath inlet.

The foregoing and other objects and features of the present invention will become apparent from the following description with reference to the attached drawings.

BRIEF DESCRIPTION OF DRAWINGS

Hereinafter, concentration of $^{12}CO_2$ is called "$^{12}$Conc", concentration of $^{13}CO_2$ is called "$^{13}$Conc", absorbance of $^{12}CO_2$ is called "$^{12}$Abs" and absorbance of $^{13}CO_2$ is called "$^{13}$Abs".

FIGS. 10A and 10B are a plan view and a side view, respectively, of a gas injector for quantitatively injecting a gaseous sample;

FIG. 17A is a graphical representation in which $^{12}CO_2$ concentrations and $^{12}CO_2$ absorbances are plotted as abscissa and ordinate, respectively, for preparation of a calibration curve, the $^{12}CO_2$ absorbances having been measured for 20 measuring points in a $^{12}CO_2$ concentration range of about 0% to about 6%;

FIG. 17B is a graphical representation in which $^{12}CO_2$ concentrations and $^{12}CO_2$ absorbances in five data points in a relatively narrow $^{12}CO_2$ concentration range around a $^{12}CO_2$ concentration determined by using the calibration curve of FIG. 17A are plotted as abscissa and ordinate, respectively;

FIG. 18A is a graphical representation in which $^{13}CO_2$ concentrations and $^{13}CO_2$ absorbances are plotted as abscissa and ordinate, respectively, for preparation of a calibration curve, the $^{13}CO_2$ absorbances having been measured for 20 measuring points in a $^{13}CO_2$ concentration range of about 0.00% to about 0.07%;

FIG. 18B is a graphical representation in which $^{13}CO_2$ concentrations and $^{13}CO_2$ absorbances in five data points in a relatively narrow $^{13}CO_2$ concentration range around a $^{13}CO_2$ concentration determined by using the calibration curve of FIG. 18A are plotted as abscissa and ordinate, respectively;

FIG. 20 is a graphical representation illustrating the relationship of $^{12}Conc$ (plotted as abscissa) versus $^{13}CO_2$ concentration ratio $^{13}Conc/^{12}Conc$ (plotted as ordinate) which was determined by measuring the $^{12}CO_2$ concentrations $^{12}Conc$ and $^{13}CO_2$ concentrations $^{13}Conc$ of gaseous samples;

FIG. 22 is a graphical representation illustrating the relationship of $^{12}Conc$ (plotted as abscissa) versus concentration ratio $^{13}Conc/^{12}Conc$ (plotted as ordinate) which was obtained by determining the $^{12}CO_2$ concentrations $^{12}Conc$ and $^{13}CO_2$ concentrations $^{13}Conc$ of gaseous samples on the basis of absorbances measured on the gaseous samples by using the calibration curves shown in FIGS. 17A and 18A;

FIG. 23 is a graphical representation illustrating the relationship of $^{12}Conc$ (plotted as abscissa) and concentration ratio $^{13}Conc/^{12}Conc$ (plotted as ordinate) which was obtained by determining the concentration ratios $^{13}Conc/^{12}Conc$ of gaseous samples first on the basis of the calibration curves shown in FIGS. 17A and 18A and then on the basis of the calibration curves in limited ranges shown in FIGS. 17B and 18B.

BEST MODE FOR CARRYING OUT THE INVENTION

A preferred embodiment of the present invention will hereinafter be described with reference to the attached drawings. The embodiment is adapted for a case where a $^{13}CO_2$ concentration or concentration ratio $^{13}Conc/^{12}Conc$ in a breath test sample is spectrometrically determined after administration of an urea diagnostic drug labeled with an isotope $^{13}C$.

I. Breath Test

Before the urea diagnostic drug is administered to a patient, breath of the patient is sampled in a breath sampling bag. The volume of the breath sampling bag may be about 250 ml. Then, the urea diagnostic drug is administered to the patient and, after a lapse of 10 to 15 minutes, breath of the patient is sampled in the breath sampling bag in the same manner as in the previous breath sampling.

Figure 5:
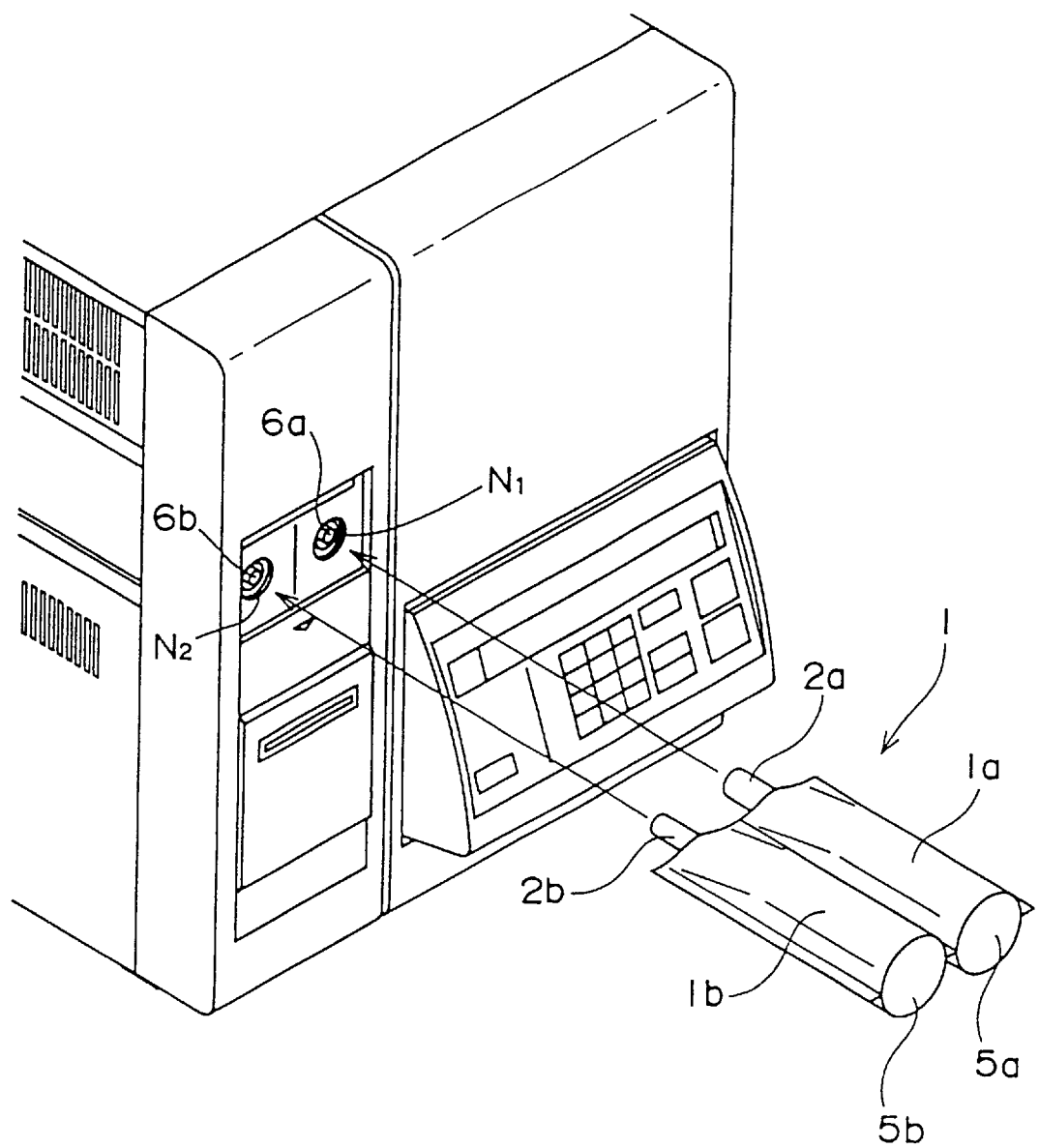
FIG. 5 is a view illustrating the appearance of a breath sampling bag to be connected to nozzles of an apparatus for spectrometrically measuring an isotopic gas.

FIG. 5 is a view illustrating the appearance of the breath sampling bag 1 to be connected to nozzles $N_1$ and $N_2$ Of an apparatus for spectrometrically measuring an isotopic gas. The breath sampling bag 1 includes a breath sampling chamber 1a for sampling breath of the patient after the administration of the urea diagnostic drug and a breath sampling chamber 1b for sampling breath of the patient before the administration of the urea diagnostic drug, the breath sampling chambers 1a and 1b being integrally molded and joined together to form a single body.

A pipe 2a is attached to an end of the breath sampling chamber 1a, and a pipe 2b is attached to an end of the breath sampling chamber 1b. Bottom ends 5a and 5b of the breath sampling chambers 1a and 1b are closed. The pipes 2a and 2b each have two functions, i.e., the pipes 2a and 2b serve not only as breath blowing ports from which breath is blown into the breath sampling chambers 1a and 1b, but also for introducing the breath samples from the breath sampling chambers 1a and 1b into the spectrometric apparatus when the breath sampling bag is connected to the nozzles $N_1$ and $N_2$ of the apparatus.

When breath is sampled, a cylindrical filter (like cigarette filter) 7a or 7b is fitted into the pipe 2a or 2b, and then the breath is blown into the breath sampling bag 1. The filters 7a and 7b are used to remove moisture in the breath.

Figure 6:
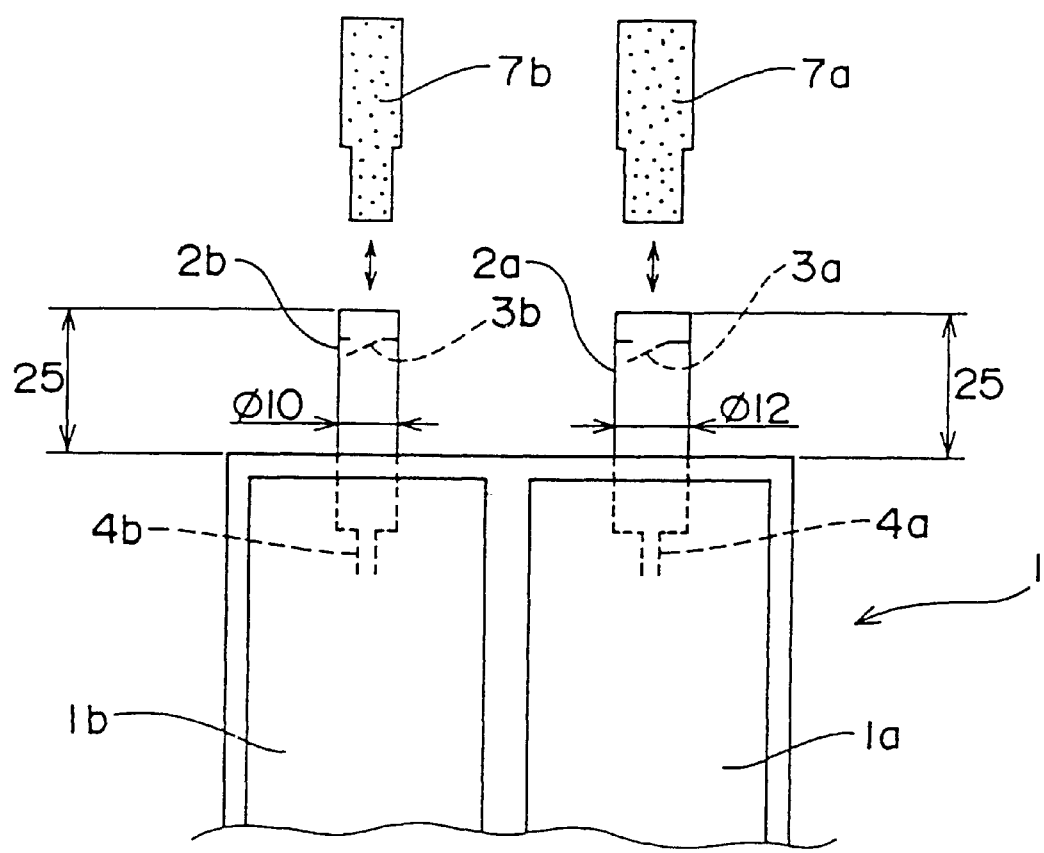
FIG. 6 is a partial view illustrating pipes connected to an end of the breath sampling bag.

As shown in FIG. 6, back-flow valves 3a and 3b are provided in the pipes 2a and 2b, respectively, for preventing the breath blown into the breath sampling bag from flowing back.

The pipes 2a and 2b each have a portion having a smaller inner diameter (e.g., a smaller diameter portion 4a or 4b) for generating a resistance to the blowing of the breath. The resistance to the blowing of the breath allows the patient to exhale air from his lung. It has been experimentally confirmed that air exhaled from the lung of a patient provides a more stable $CO_2$ concentration than air present in the oral cavity of the patient.

After the completion of the sampling of the breath, the filters are removed, and the pipes 2a and 2b are inserted into the nozzles $N_1$ and $N_2$, respectively, of the spectrometric apparatus. The nozzles $N_1$ and $N_2$ have different inner diameters, and the pipes 2a and 2b have different outer diameters corresponding to the inner diameters of the nozzles $N_1$ and $N_2$. This prevents the pipes 2a and 2b from being inserted into wrong nozzles $N_2$ and $N_1$, thereby preventing the breath samples obtained before and after the administration of the urea diagnostic drug from being mistakenly manipulated.

The nozzles $N_1$ and $N_2$ of the spectrometric apparatus have projections 6a and 6b, respectively, which are adapted to disable the function of the back-flow valves 3a and 3b when the pipes 2a and 2b are inserted into the nozzles $N_1$ and $N_2$.

Although the outer diameters of the pipes 2a and 2b are made different in this embodiment, any other constructions may be employed to prevent the mistake of connection between the pipes 2a and 2b and the nozzles $N_1$ and $N_2$. For example, the pipes may have different lengths and the nozzles $N_1$ and $N_2$ of the spectrometric apparatus may have different depths corresponding to the lengths of the pipes. With this construction, a longer one of the pipes mistakenly inserted into a nozzle having a smaller depth fails to perfectly fit in the nozzle. Therefore, a user notices the connection mistake of the pipes. Alternatively, the pipes may have different cross sections (e.g., round, rectangular or triangular cross sections).

Upon completion of the connection of the breath sampling bag 1, the spectrometric apparatus performs the following automatic control.

II. Apparatus for Spectrometrically Measuring Isotopic Gas

Figure 7:
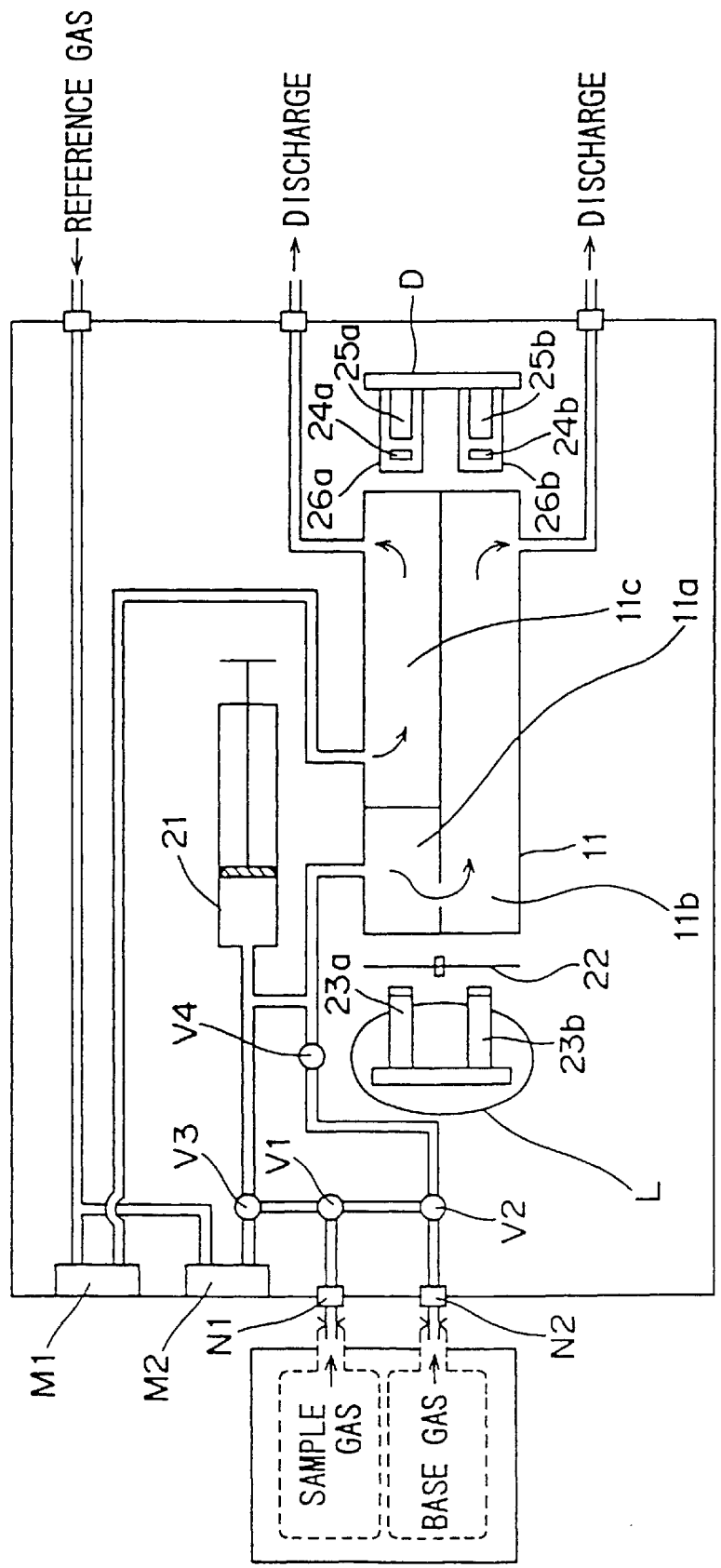
FIG. 7 is a block diagram illustrating the overall construction of the spectrometric apparatus.

FIG. 7 is a block diagram illustrating the overall construction of the apparatus for spectrometrically measuring an isotopic gas.

The breath sampling bag is set to the apparatus so that one breath sampling chamber thereof containing the breath sampled after the drug administration (hereinafter referred to as "sample gas") and the other breath sampling chamber thereof containing the breath (hereinafter referred to as "base gas") sampled before the drug administration are connected to the nozzles $N_1$ and $N_2$, respectively. The nozzle $N_1$ is connected to one port of a three-way valve $V_1$ through a transparent resin pipe (hereinafter referred to simply as "pipe") and the nozzle $N_2$ is connected to one port of a three-way valve $V_2$ through a pipe.

A reference gas (any gas having no absorption at a wavelength for measurement, e.g., nitrogen gas) is supplied from a gas cylinder to the apparatus. The reference gas flows through a flow path diverged into two paths. One path is connected through a flow meter $M_1$ to a reference cell 11*c*. The other path is connected through a flow meter $M_2$ to one port of a three-way valve $V_3$. The reference gas flows into the reference cell 11*c*, and discharged therefrom.

The other ports of the three-way valve $V_3$ are connected to another port of the three-way valve $V_1$ and to a first sample cell 11*a* for measuring a $^{12}CO_2$ absorbance. The other ports of the three-way valve $V_2$ are connected to the first sample cell 11*a* through a two-way valve $V_4$ and to the other port of the three-way valve $V_1$.

A gas injector 21 (volume: 60 cc) for quantitatively injecting the sample gas or the base gas is interposed between the three-way valve $V_3$ and the first sample cell 11*a*. The gas injector 21 is a syringe-like device having a piston and a cylinder. The piston is driven by cooperation of a motor, a screw connected to the motor and a nut fixed to the piston (which will be described later).

As shown in FIG. 7, a cell chamber 11 has the first sample cell 11*a* having a smaller length for measuring therein a $^{12}CO_2$ absorbance, a second sample cell 11*b* having a greater length for measuring therein a $^{13}CO_2$ absorbance, and the reference cell 11*c* through which the reference gas is passed. The first sample cell 11*a* communicates with the second sample cell 11*b*. The sample gas or the base gas is introduced into the first sample cell 11*a* and then into the second cell 11*b*, and discharged therefrom. The reference gas is introduced into the reference cell 11*c*, and then discharged therefrom. Specifically, the first and second sample cells 11*a* and 11*b* have lengths of 13 mm and 250 mm, respectively, and the reference cell 11*c* has a length of 236 mm.

A discharge pipe extending from the second sample cell 11*b* is provided with an $O_2$ sensor 18. Usable as the $O_2$ sensor 18 are commercially available oxygen sensors such as a solid lectrolyte gas sensor (e.g., zirconia sensor) and an electrochemical gas sensor (e.g., galvanic cell sensor).

Figure 8:
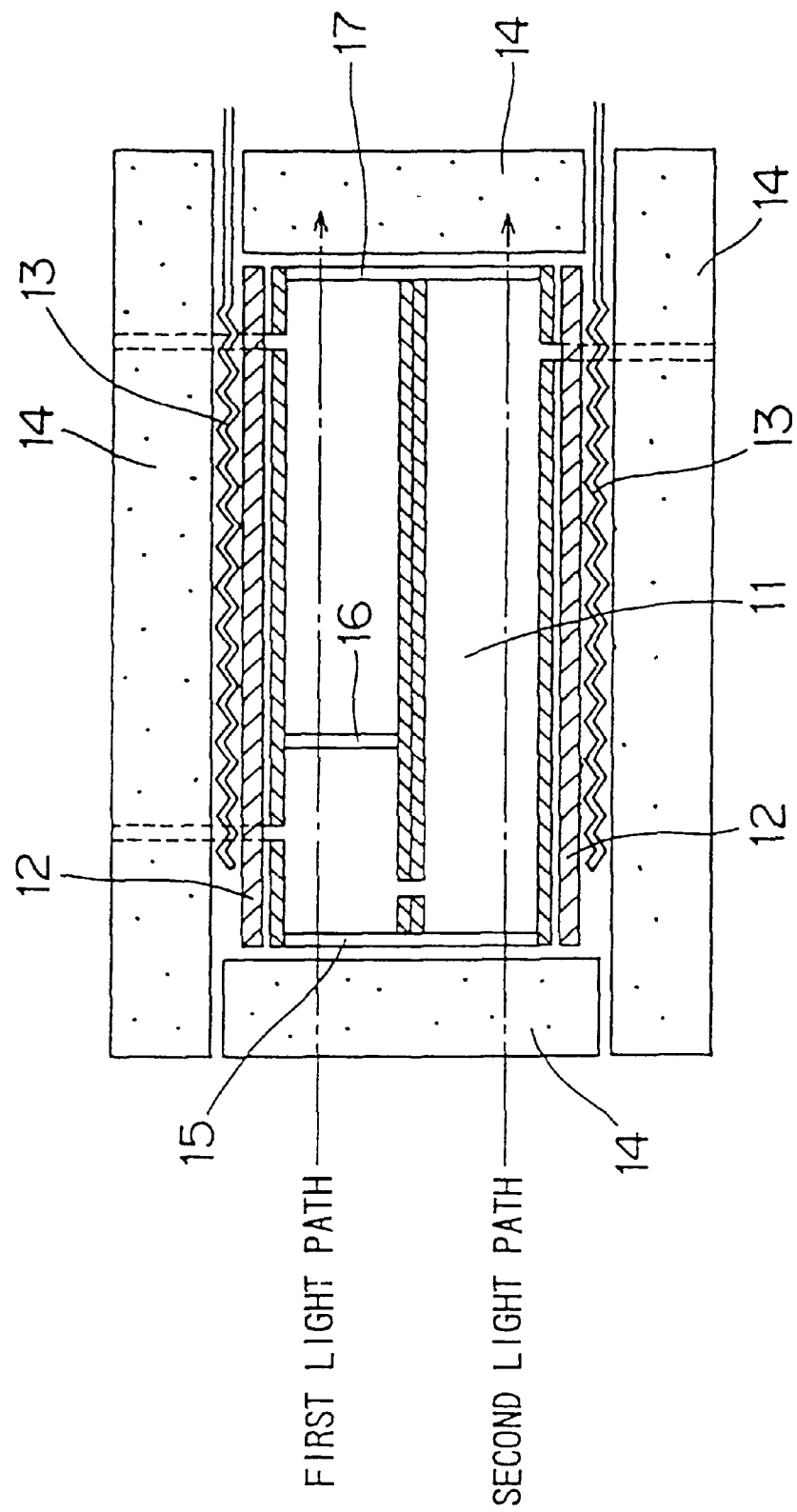
FIG. 8 is a sectional view illustrating the construction of a cell chamber 11.

A reference character L denotes an infrared light source having two waveguides 23*a* and 23*b* for guiding infrared rays or irradiation. The generation of the infrared rays may be achieved in any way. For example, a ceramic heater (surface temperature: 450° C.) and the like can be used. A rotary chopper 22 for periodically blocking the infrared rays is provided adjacent to the infrared light source L. Infrared rays emitted from the infrared light source L are transmitted to the first sample cell 11*a* and the reference cell 11*c* through a first light path, and to the second sample cell 11*b* through a second light path (see FIG. 8).

A reference character D denotes an infrared detector for detecting the infrared rays transmitted through the cells. The infrared detector D has a first wavelength filter 24*a* and a first detection element 25*a* disposed in the first light path, and a second wavelength filter 24*b* and a second detection element 25*b* disposed in the second light path.

The first wavelength filter 24*a* (band width: about 20 nm) passes an infrared ray having a wavelength of about 4,280 nm to be used for measurement of a $^{12}CO_2$ absorbance. The second wavelength filter 24*b* (band width: about 50 nm) passes an infrared ray having a wavelength of about 4,412 nm to be used for measurement of a $^{13}CO_2$ absorbance. Usable as the first and second detection elements 25*a* and 25*b* are any elements capable of detecting infrared rays. For example, a semiconductor infrared sensor such as of PbSe is used.

The first wavelength filter 24*a* and the first detection element 25*a* are housed in a package 26*a* filled with an inert gas such as Ar. Similarly, the second wavelength filter 24*b* and the second detection element 25*b* are housed in a package 26*b* filled with an inert gas.

The whole infrared detector D is maintained at a constant temperature (25° C.) by means of a heater and a Peltier element. The inside temperatures of the packages 26*a* and 26*b* are kept at 0° C. by means of a Peltier element.

The cell chamber 11 is formed of a stainless steel, and vertically and laterally sandwiched between metal plates (e.g., brass plates) 12. A heater 13 is provided on upper, lower and lateral sides of the cell chamber. The cell chamber 11 is sealed with insulators 14 such as of polystyrene foam with the heater 13 interposed therebetween. Though not shown, a temperature sensor (e.g., a platinum temperature sensor) for measuring the temperature of the cell chamber 11 is provided in the cell chamber 11.

The cell chamber 11 has two tiers. The first sample cell 11*a* and the reference cell 11*c* are disposed in one tier, and the second sample cell 11*b* is disposed in the other tier.

The first light path extends through the first sample cell 11*a* and the reference cell 11*c* which are disposed in series, and the second light path extends through the second sample cell b. Reference characters 15, 16 and 17 denote sapphire transmission windows through which the infrared rays are transmitted.

Figure 9:
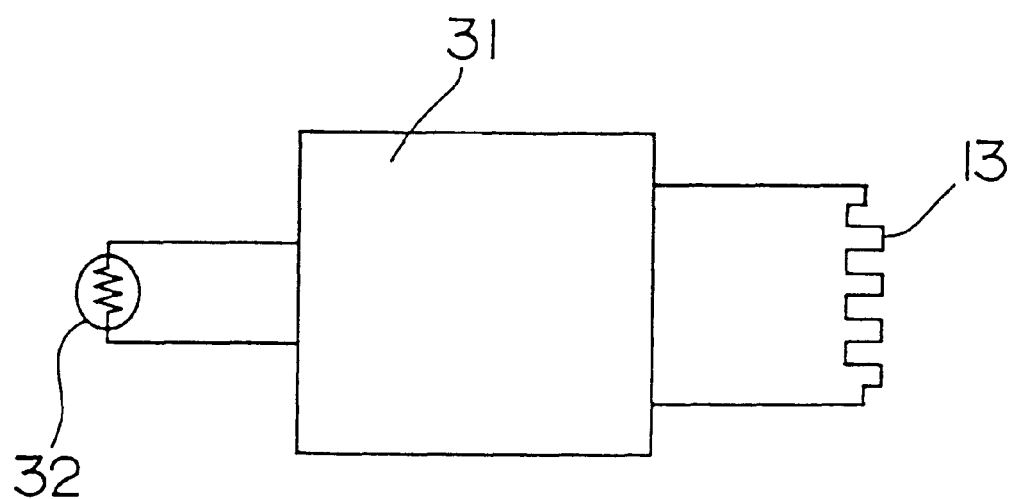
FIG. 9 is a block diagram schematically illustrating a mechanism for adjusting the temperature of the cell chamber.

FIG. 9 is a block diagram illustrating a mechanism for adjusting the temperature of the cell chamber 11. The temperature adjustment mechanism is constituted by the temperature sensor 32 provided in the cell chamber 11, a temperature adjustment substrate 31 and the heater 13. The temperature of the temperature adjustment substrate 31 may be adjusted in any manner. For example, the temperature adjustment can be achieved by changing the duty ratio of a pulse current flowing through the heater 13 on the basis of a temperature measurement signal of the temperature sensor 32. The heater 13 is controlled on the basis of this temperature adjustment method so as to maintain the cell chamber 11 at a constant temperature (40° C.).

FIGS. 10A and 10B are a plan view and a side view, respectively, of the gas injector 21 for quantitatively injecting a gaseous sample.

The gas injector 21 includes a cylinder 21*b* disposed on a base 21*a*, a piston 21*c* inserted in the cylinder 21*c*, and a movable nut 21*d* connected to the piston 21*c*, a feed screw 21*e* threadingly meshed with the nut 21*d* and a motor 21*f* for rotating the feed screw 21*e* which are disposed below the base 21*a*.

The motor 21$f$ is driven for forward and backward rotation by a driving circuit not shown. As the feed screw 21$e$ is rotated by the rotation of the motor 21$f$, the nut 21$d$ moved forward or backward depending on the rotational direction of the feed screw 21$e$. The piston 21$c$ advances toward a position indicated by a dashed line in FIG. 10A. Thus, the gas injector 21 can be flexibly controlled to introduce and extract the gaseous sample in/from the cylinder 21$b$.

IIIa. Measuring Procedure 1

The measuring procedure includes reference gas measurement, base gas measurement, reference gas measurement, sample gas measurement and reference gas measurement, which are to be performed in this order. Alternatively, base gas measurement, reference gas measurement and base gas measurement, and sample gas measurement, reference gas measurement and sample gas measurement may be performed in this order. In the latter case, the base gas measurement and the sample gas measurement are each performed twice and, therefore, the operation efficiency is reduced. The former measuring procedure which is more efficient will hereinafter be described.

During the measurement, the reference gas constantly flows through the reference cell 11$c$, and the flow rate hereof is always kept constant by the flow meter $M_1$.

III a-1. Reference Measurement

Figure 11:
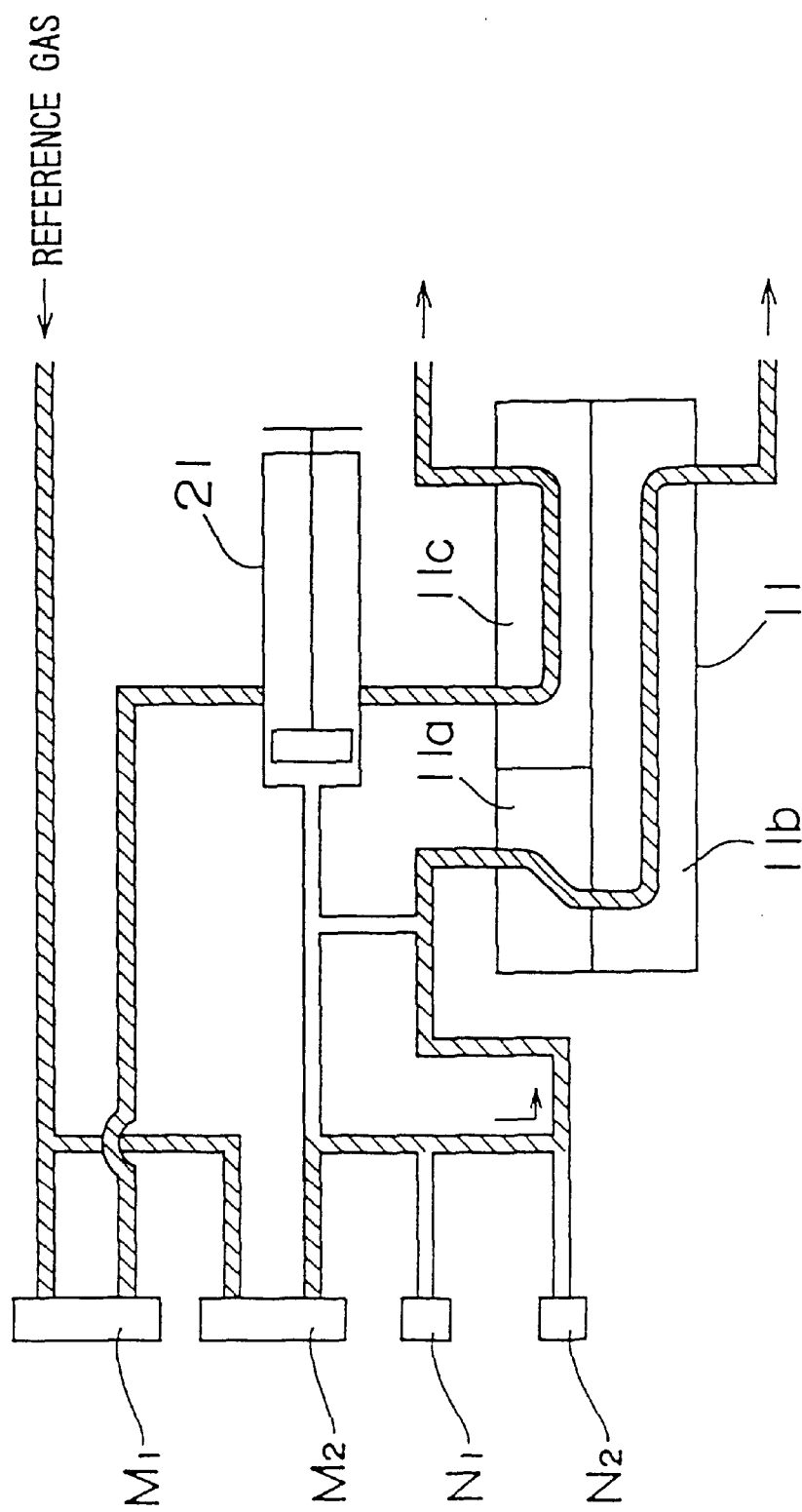
FIG. 11 is a diagram illustrating a gas flow path through which a clean reference gas is passed for cleaning the gas flow path and the cell chamber of the spectrometric apparatus.

As shown in FIG. 11, the clean reference gas is passed through a gas flow path and the cell chamber 11 of the spectrometric apparatus at a rate of 200 ml/minute for about 15 seconds for cleaning the gas flow path and the cell chamber 11.

Figure 12:
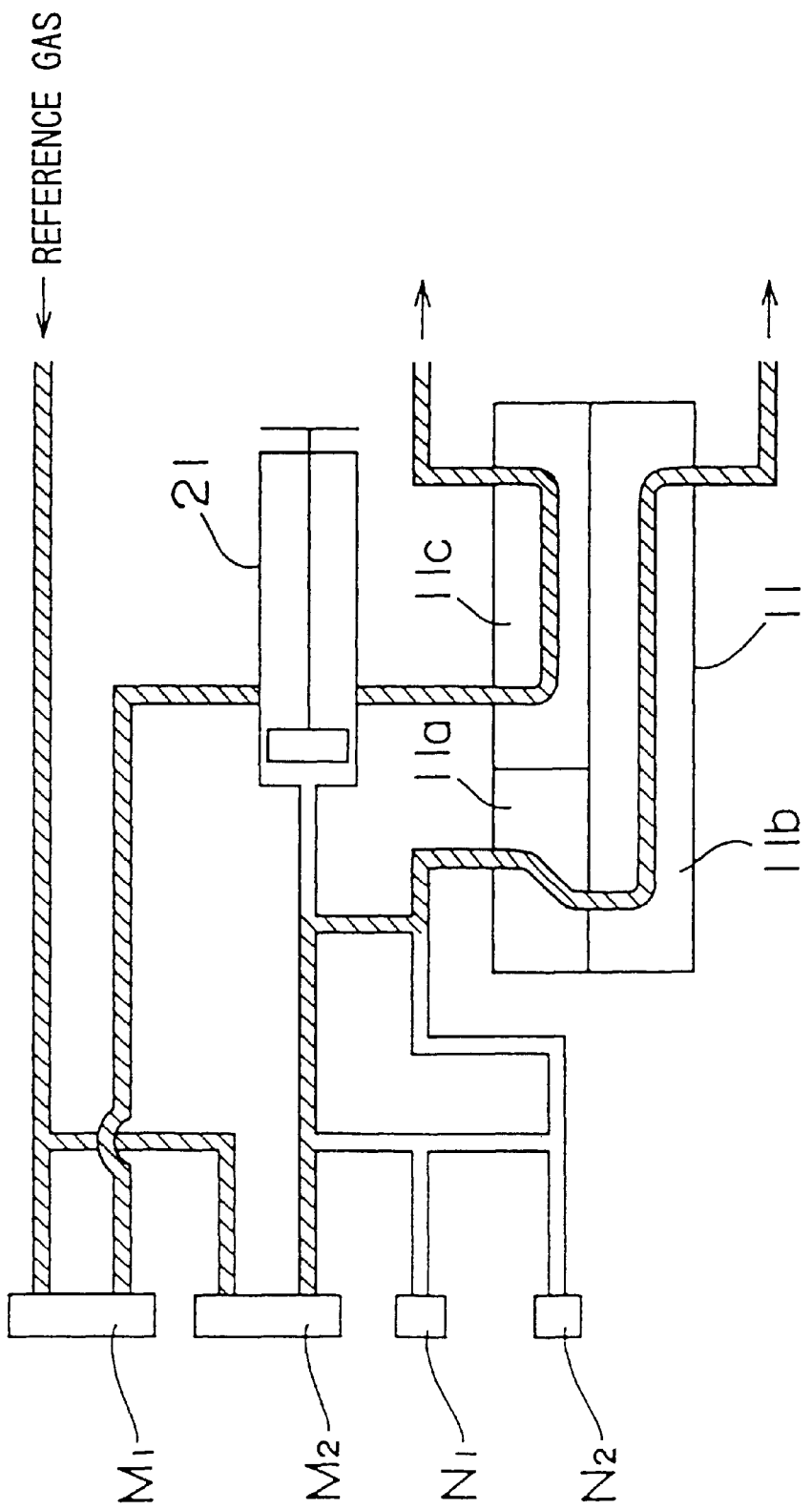
FIG. 12 is a diagram illustrating a gas flow path through which the clean reference gas is passed for cleaning the gas flow path and the cell chamber of the spectrometric apparatus and for performing a reference measurement.

In turn, as shown in FIG. 12, the gas flow path is changed, and then the reference gas is passed therethrough for cleaning the gas flow path and the cell chamber 11. After a lapse of about 30 seconds, light intensity are measured by means of the detection elements 25$a$ and 25$b$.

On the basis of the reference measurement, absorbances are calculated.

The light intensity thus obtained by the first and second detection elements 25$a$ and 25$b$ are represented by $^{12}R_1$ and $^{13}R_1$, respectively.

IIIa-2. Base Gas Measurement

Figure 13:
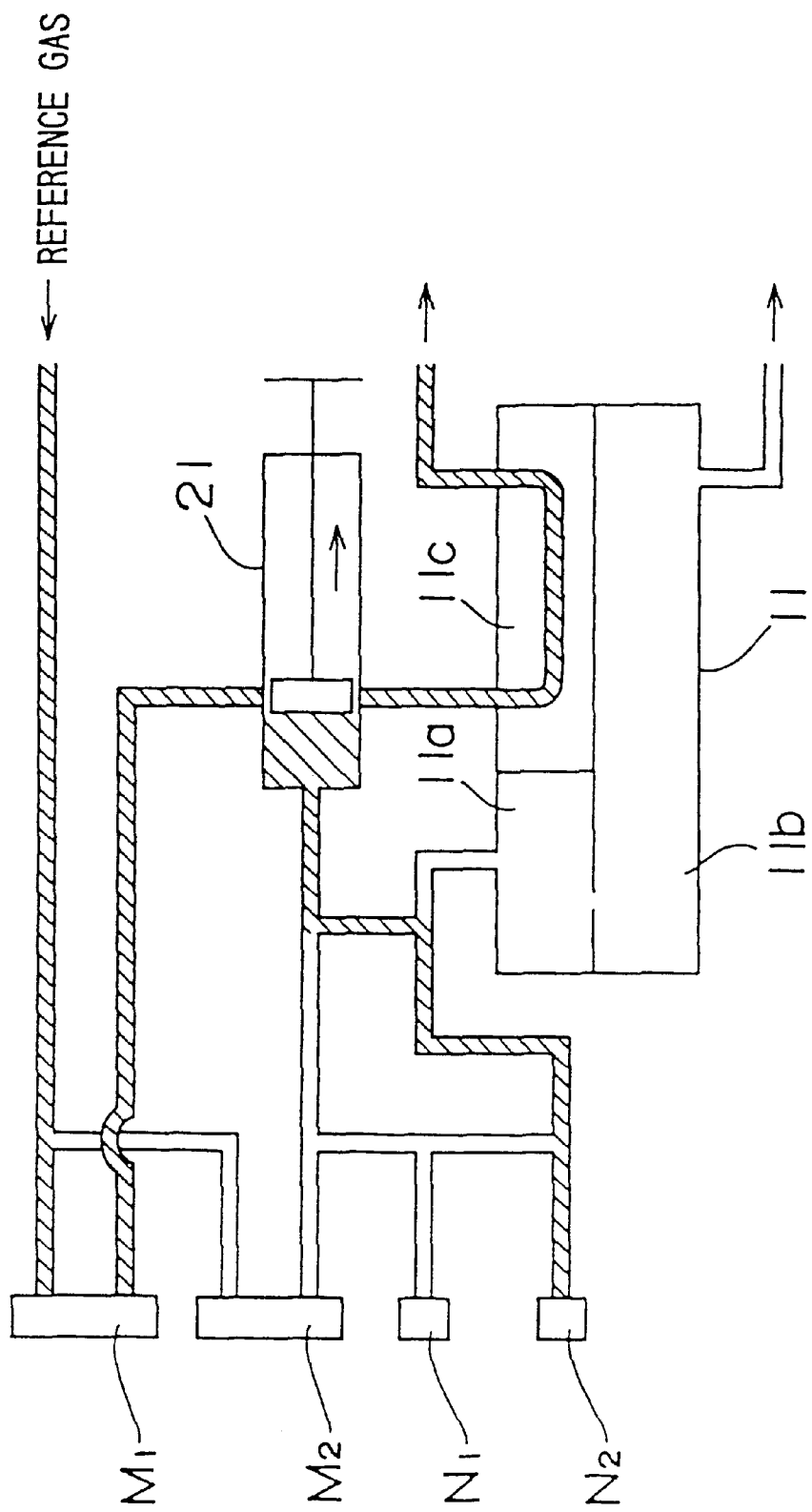
FIG. 13 is a diagram illustrating a state where a base gas is sucked from a breath sampling bag by means of the gas injector 21 with the reference gas prevented from flowing through first and second sample cells 11a and 11b.

The base gas is sucked into the gas injector 21 from the breath sampling bag with the reference gas prevented from flowing through the first and second sample cells 11$a$ and 11$b$ (see FIG. 13).

Figure 14:
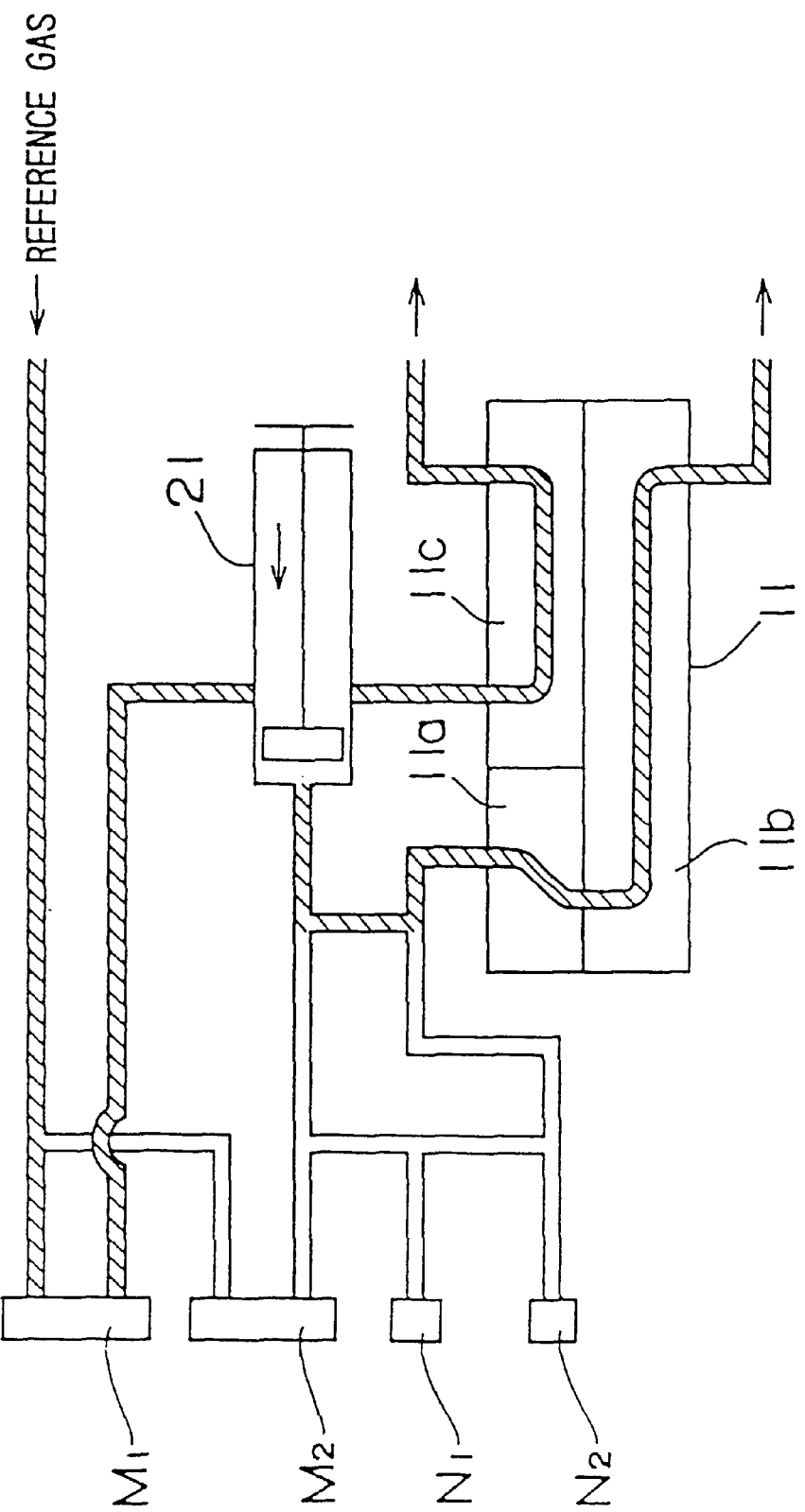
FIG. 14 is a diagram illustrating a gas flow path to be employed when the base gas sucked in the gas injector 21 is mechanically pushed out at a constant rate by the gas injector 21 for measurement of light intensity by detection elements 25a and 25b.

Thereafter, the base gas is mechanically pushed out at a constant rate (60 ml/minute) by the gas injector 21 as shown in FIG. 14 and, at the same time, light intensity are measured by means of the detection elements 25$a$ and 25$b$.

The light intensity thus obtained by the first and second detection elements 25$a$ and 25$b$ are represented by $^{12}B$ and $^{13}B$, respectively.

IIIa-3. Reference Measurement

The cleaning of the gas flow path and the cells and the light intensity measurement on the reference gas are performed again (see FIGS. 11 and 12).

The light intensity thus obtained by the first and second detection elements 25$a$ and 25$b$ are represented by $^{12}R_2$ and $^{13}R_2$, respectively.

IIIa-4. Sample Gas Measurement

Figure 15:
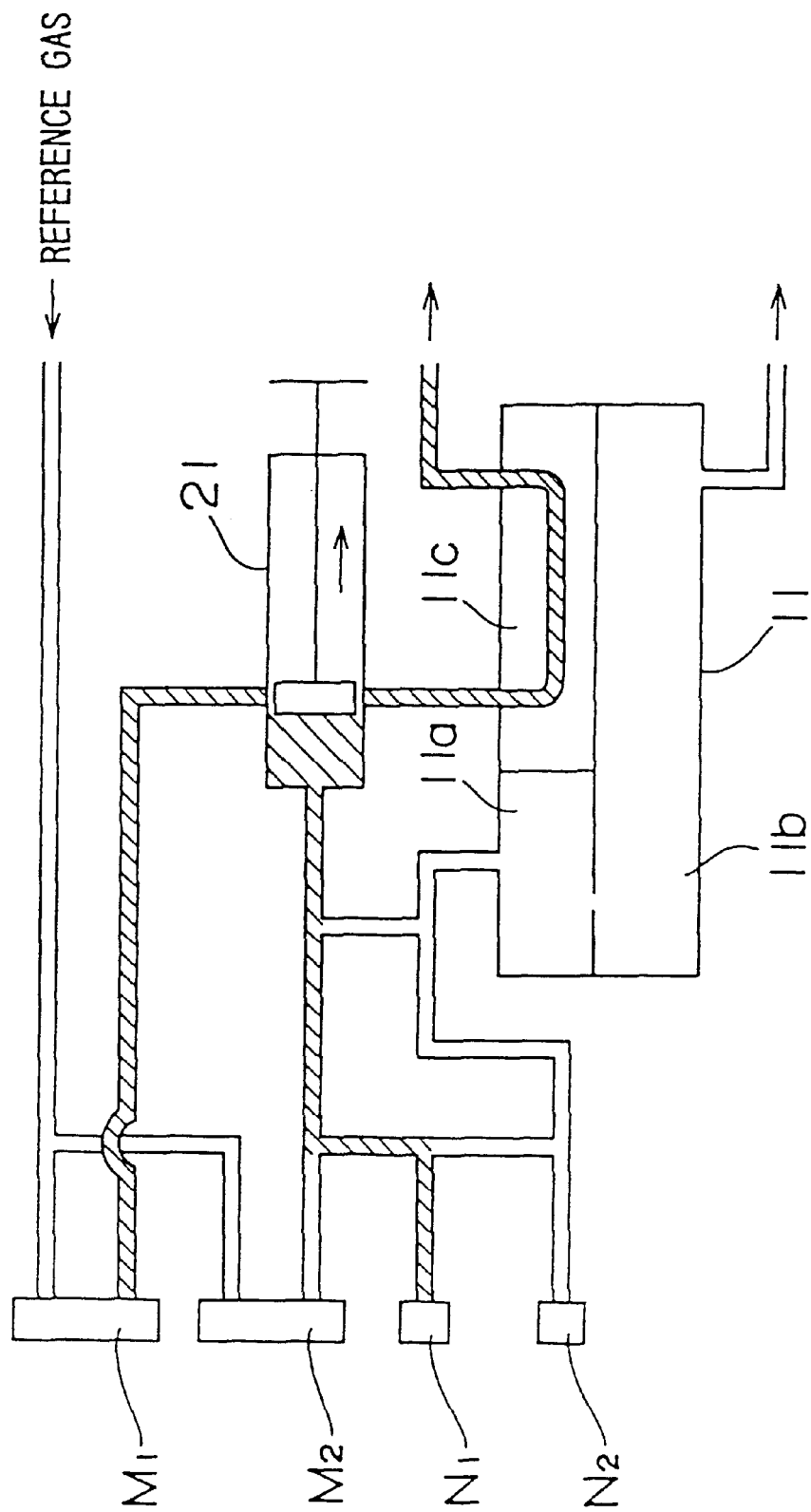
FIG. 15 is a diagram illustrating a state where a sample gas is sucked from the breath sampling bag by means of the gas injector 21 with the reference gas prevented from flowing through the first and second sample cells 11a and 11b.

The sample gas is sucked into the gas injector 21 from the breath sampling bag with the reference gas prevented from flowing through the first and second sample cells 11$a$ and 11$b$ (see FIG. 15).

Figure 16:
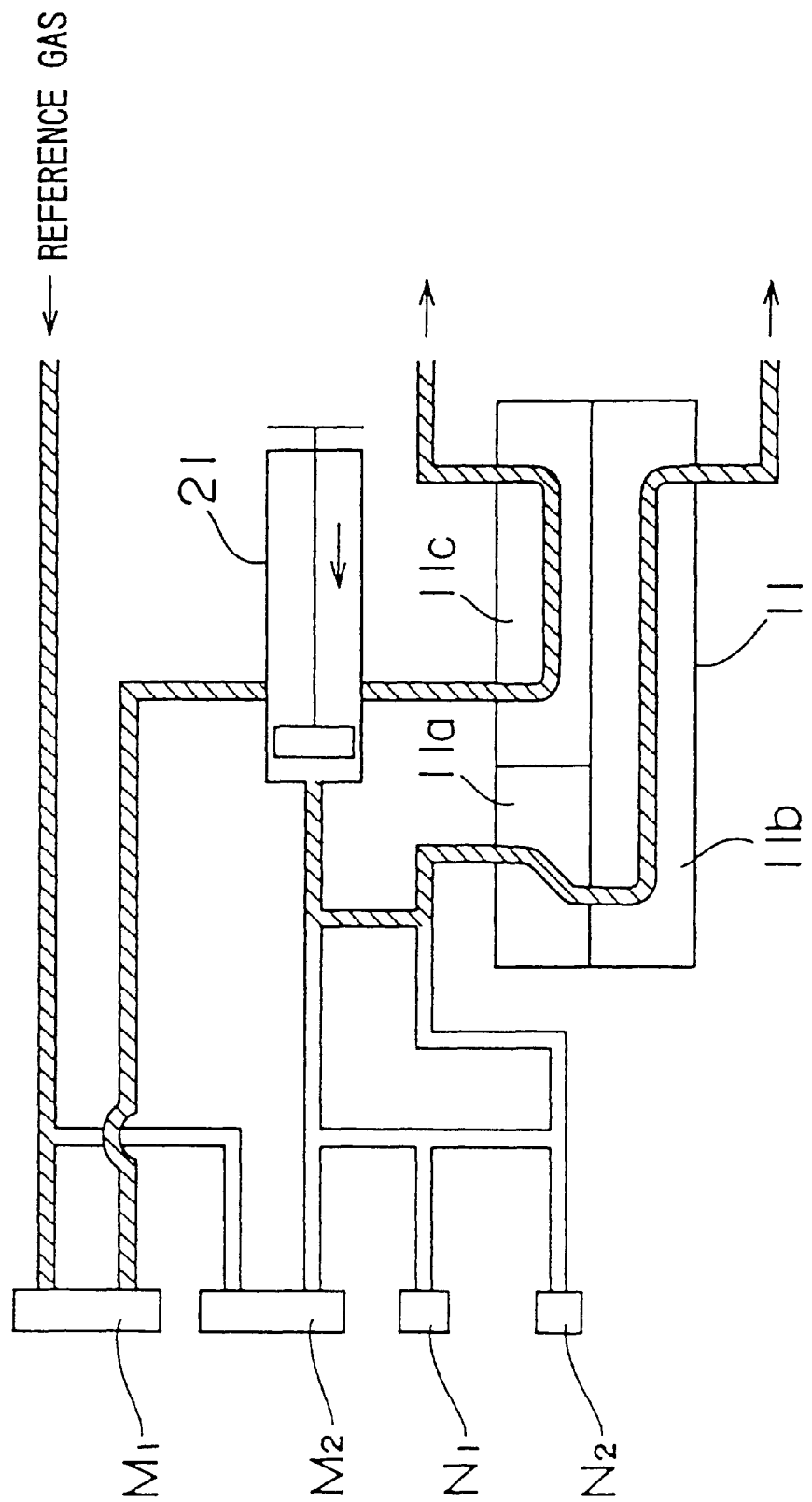
FIG. 16 is a diagram illustrating a gas flow path to be employed when the sample gas sucked in the gas injector 21 is mechanically pushed out at a constant rate by the gas injector 21 for measurement of light intensity by the detection elements 25a and 25b.

Thereafter, the sample gas is mechanically pushed out at a constant rate (60 ml/minute) by the gas injector 21 as shown in FIG. 16 and, at the same time, light intensity are measured by means of the detection elements 25$a$ and 25$b$.

The light intensity thus obtained by the first and second detection elements 25$a$ and 25$b$ are represented by $^{12}S$ and $^{13}S$, respectively.

IIIa-5. Reference Measurement

The cleaning of the gas flow path and the cells and the light intensity measurement on the reference gas are performed again (see FIGS. 11 and 12).

The light intensity thus obtained by the first and second detection elements 25$a$ and 25$b$ are represented by $^{12}R_3$ and $^{13}R_3$, respectively.

IIIb. Measurement Procedure 2

In the measurement procedure 1, the $CO_2$ concentrations of the base gas and the sample gas are not adjusted to the same level.

If the base gas and the sample gas are at the same $CO_2$ concentration level, the ranges of $^{12}CO_2$ and $^{13}CO_2$ calibration curves to be used for determination of the concentrations can be narrowed. By using limited ranges of the calibration curves, the measurement accuracy can be increased.

In accordance with the measurement procedure 2, the $CO_2$ concentrations of the base gas and the sample gas are adjusted to substantially the same level. First, the $CO_2$ concentrations of the base gas and the sample gas are measured in a preliminary measurement. If the $CO_2$ concentration of the base gas obtained in the preliminary measurement is higher than the $CO_2$ concentration of the sample gas obtained in the preliminary measurement, the base gas is diluted to a $CO_2$ concentration level equivalent to that of the sample gas, and the measurement of the concentration is performed on the base gas and then on the sample gas in a main measurement.

If the $CO_2$ concentration of the base gas obtained in the preliminary measurement is lower than the $CO_2$ concentration of the sample gas obtained in the preliminary measurement, the $CO_2$ concentration of the base gas is measured in the main measurement. The sample gas is diluted to a $CO_2$ concentration level equivalent to that of the base gas, and then the $CO_2$ concentration thereof is measured.

The measurement procedure 2 includes preliminary base gas measurement, preliminary sample gas measurement, reference gas measurement, base gas measurement, reference gas measurement, sample gas measurement and reference gas measurement, which are performed in this order.

IIIb-1. Preliminary Base Gas Measurement

The clean reference gas is passed through the gas flow path and the cell chamber 11 of the spectrometric apparatus for cleaning the gas flow path and the cell chamber 11 and, at the same time, a reference light intensity is measured.

In turn, the base gas is sucked into the gas injector 21 from the breath sampling bag, and then mechanically pushed out at a constant flow rate by means of the gas injector 21. At this time, the intensity of light transmitted through the base gas is measured by means of the detection element 25$a$ to determine an absorbance, and the $CO_2$ concentration of the base gas is determined on the basis of the absorbance by using a calibration curve.

IIIb-2. Preliminary Sample Gas Measurement

The clean reference gas is passed through the gas flow path and the cell chamber 11 of the spectrometric apparatus for cleaning the gas flow path and the cell chamber 11 and, at the same time, a reference light intensity is measured.

In turn, the sample gas is sucked into the gas injector 21 from the breath sampling bag, and then mechanically pushed out at a constant flow rate by means of the gas injector 21. At this time, the intensity of light transmitted through the sample gas is measured by means of the detection element 25a to determine an absorbance, and the $CO_2$ concentration of the sample gas is determined on the basis of the absorbance by using the calibration curve.

IIIb-3. Reference Measurement

The gas flow path is changed, and then the reference gas is passed therethrough to clean the gas flow path and the cell chamber 11. After a lapse of about 30 seconds, light intensity are measured by means of the detection elements 25a and 25b.

The light intensity thus obtained by the first and second detection elements 25a and 25b are represented by $^{12}R_1$ and $^{13}R_1$, respectively.

IIIb-4. Base Gas Measurement

The $CO_2$ concentration of the base gas obtained by the first detection element 25a in "IIIb-1. Preliminary base gas measurement" is compared with the $CO_2$ concentration of the sample gas obtained by the first detection element 25a in "IIIb-2. Preliminary sample gas measurement". If the $CO_2$ concentration of the base gas is higher than the $CO_2$ concentration of the sample gas, the base gas is diluted with the reference gas in the gas injector 21 to a $CO_2$ concentration level equivalent to that of the sample gas, and then the light intensity measurement is performed on the base gas thus diluted.

Since the $CO_2$ concentrations of the two breath samples are adjusted to substantially the same level by dilution, the ranges of the $^{12}CO_2$ and $^{13}CO_2$ calibration curves to be used can be narrowed.

It should be noted that the measuring procedure 2 of this embodiment is characterized in that the $CO_2$ concentrations of the two breath samples are adjusted to substantially the same level, and does not necessarily require to employ a step of maintaining the $CO_2$ concentration at a constant level as described in JPB 4(1992)-124141. The use of limited ranges of calibration curves can be achieved simply by adjusting the $CO_2$ concentrations of the base gas and the sample gas to substantially the same level. Since the $CO_2$ concentrations of the base gas and the sample gas vary within a range of 1% to 5% in actual measurement, it is very troublesome to always maintain the $CO_2$ concentrations at a constant level.

If the $CO_2$ concentration of the base gas is lower than the $CO_2$ concentration of the sample gas, the base gas is not diluted, and the measurement is performed on the base gas.

The base gas is mechanically pushed out at a constant flow rate by the gas injector 21, and light intensity are measured by means of the detection elements 25a and 25b.

The light intensity thus obtained by the first and second detection elements 25a and 25b are represented by $^{12}B$ and $^{13}B$, respectively.

IIIb-5. Reference Measurement

The cleaning of the gas flow path and the cells and the light intensity measurement on the reference gas are performed again.

The light intensity thus obtained by the first and second detection elements 25a and 25b are represented by $^{12}R_2$ and $^{13}R_2$, respectively.

IIIb-6. Sample Gas Measurement

If the base gas is diluted in "IIIb-4. Base gas measurement", the sample gas is sucked from the breath sampling bag, and then mechanically pushed out at a constant flow rate by the gas injector 21. At this time, light intensity are measured by the detection elements 25a and 25b.

If the base gas is not diluted in "IIIb-4. Base gas measurement", the sample gas is diluted with the reference gas to a $CO_2$ concentration level equivalent to that of the base gas in the gas injector 21, and then the intensity of light transmitted through the sample gas is measured by means of the detection elements 25a and 25b.

The light intensity thus obtained by the first and second detection elements 25a and 25b are represented by $^{12}S$ and $^{13}S$, respectively.

IIIb-7. Reference Measurement

The cleaning of the gas flow path and the cells and the light intensity measurement on the reference gas are performed again.

The light intensity thus obtained by the first and second detection elements 25a and 25b are represented by $^{12}R_3$ and $^{13}R_3$, respectively.

IV. Data Processing

IV-1. Calculation of Absorbances for Base Gas

Absorbances $^{12}Abs(B)$ and $^{13}Abs(B)$ of $^{12}CO_2$ and $^{13}CO_2$ in the base gas are calculated on the basis of the transmitted light intensity $^{12}R_1$, $^{13}R_1$, $^{12}R_2$ and $^{13}R_2$ for the reference gas and the transmitted light intensity $^{12}B$ and $^{13}B$ for the base gas obtained in the measuring procedure 1 or in the measuring procedure 2.

The absorbance $^{12}Abs(B)$ of $^{12}CO_2$ is calculated from the following equation:

$$^{12}Abs(B) = -\log[2 \cdot {}^{12}B/({}^{12}R_1 + {}^{12}R_2)]$$

The absorbance $^{13}Abs(B)$ of $^{13}CO_2$ is calculated from the following equation:

$$^{13}Abs(B) = -\log[2 \cdot {}^{13}B/({}^{13}R_1 + {}^{13}R_2)]$$

Since the calculation of the absorbances is based on the light intensity obtained in the base gas measurement and the averages $({}^{12}R_1 + {}^{12}R_2)/2$ and $({}^{13}R_1 + {}^{13}R_2)/2$ of the light intensity obtained in the reference measurements performed before and after the base gas measurement, the influence of a drift (a time-related influence on the measurement) can be eliminated. Therefore, when the apparatus is turned on, there is no need for waiting until the apparatus reaches a thermal equilibrium (it usually takes several hours).

Where the measuring procedure of the base gas measurement, the reference gas measurement and the base gas measurement, and the sample gas measurement, the reference gas measurement and the sample gas measurement as describe at the beginning of "IIIa" is employed, the absorbance $^{12}Abs(B)$ of $^{12}CO_2$ in the base gas is calculated from the following equation:

$$^{12}Abs(B) = -\log[({}^{12}B_1 + {}^{12}B_2)/2 \cdot {}^{12}R]$$

and the absorbance $^{13}Abs(B)$ of $^{13}CO_2$ is calculated from the following equation:

$$^{13}Abs(B) = -\log[({}^{13}B_1 + {}^{13}B_2)/2 \cdot {}^{13}R]$$

wherein $^{12}R$ and $^{13}R$ are the transmitted light intensity for the reference gas, $^{12}B_1$ and $^{13}B_1$ are the transmitted light intensity for the base gas obtained before the reference gas measurement, and $^{12}B_2$ and $13B_2$ are the transmitted light intensity for the base gas obtained after the reference gas measurement.

IV-2. Calculation of Absorbances for Sample Gas

Absorbances $^{12}Abs(S)$ and $^{13}Abs(S)$ of $^{12}CO_2$ and $^{13}CO_2$ in the sample gas are calculated on the basis of the transmitted light intensity $^{12}R_2$, $^{13}R_2$, $^{12}R_3$ and $^{13}R_3$ for the reference gas and the transmitted light intensity $^{12}S$ and $^{13}S$ for the sample gas obtained in the measuring procedure 1 or in the measuring procedure 2.

The absorbance $^{12}Abs(S)$ of $^{12}CO_2$ is calculated from the following equation:

$$^{12}Abs(S) = -\log[2 \cdot {}^{12}S/({}^{12}R_2 + {}^{12}R_3)]$$

The absorbance $^{13}Abs(S)$ of $^{13}CO_2$ is calculated from the following equation:

$$^{13}Abs(S) = -\log[2 \cdot {}^{13}S/({}^{13}R_2 + {}^{13}R_3)]$$

Since the calculation of the absorbances is based on the light intensity obtained in the sample gas measurement and the averages of the light intensity obtained in the reference measurements performed before and after the sample gas measurement, the influence of a drift can be eliminated.

Where the measuring procedure of the base gas measurement, the reference gas measurement and the base gas measurement, and the sample gas measurement, the reference gas measurement and the sample gas measurement as describe at the beginning of "IIIa" is employed, the absorbance $^{12}Abs(S)$ of $^{12}CO_2$ in the sample gas is calculated from the following equation:

$$^{12}Abs(S) = -\log[({}^{12}S_1 + {}^{12}S_2)/2 \cdot {}^{12}R]$$

and the absorbance $^{13}Abs(S)$ of $^{13}CO_2$ is calculated from the following equation:

$$^{13}Abs(S) = -\log[({}^{13}S_1 + {}^{13}S_2)/2 \cdot {}^{13}R]$$

wherein $^{12}R$ and $^{13}R$ are the transmitted light intensity for the reference gas, $^{12}S_1$ and $^{13}S_1$ are the transmitted light intensity for the sample gas obtained before the reference gas measurement, and $^{12}S_2$ and $^{13}S_2$ are the transmitted light intensity for the sample gas obtained after the reference gas measurement.

IV-3. Calculation of Concentrations

The $^{12}CO_2$ concentration and the $^{13}CO_2$ concentration are calculated by using calibration curves.

The calibration curves for $^{12}CO_2$ and $^{13}CO_2$ are prepared on the basis of measurement performed by using gaseous samples of known $^{12}CO_2$ concentrations and gaseous samples of known $^{13}CO_2$ concentrations, respectively.

For preparation of the calibration curve for $^{12}CO_2$, the $^{12}CO_2$ absorbances for different $^{12}CO_2$ concentrations within a range of about 0% to about 6% are measured. The $^{12}CO_2$ concentrations and the $^{12}CO_2$ absorbances are plotted as abscissa and ordinate, respectively, and the curve is determined by the method of least squares. An approximate quadratic curve, which includes relatively small errors, is employed as the calibration curve in this embodiment.

For preparation of the calibration curve for $^{13}CO_2$, the $^{13}CO_2$ absorbances for different $^{13}CO_2$ concentrations within a range of about 0.00% to about 0.07% are measured. The $^{13}CO_2$ concentrations and the $^{13}CO_2$ absorbances are plotted as abscissa and ordinate, respectively, and the curve is determined by the method of least squares. An approximate quadratic curve, which includes relatively small errors, is employed as the calibration curve in this embodiment.

Strictly speaking, the $^{13}CO_2$ absorbance determined by individually measuring gases respectively containing $^{12}CO_2$ and $^{13}CO_2$ may be different from the $^{13}CO_2$ absorbance determined by measuring a gas containing both $^{12}CO_2$ and $^{13}CO_2$. This is because the wavelength filters each have a bandwidth and the $^{12}CO_2$ absorption spectrum partially overlaps $^{13}CO_2$ absorption spectrum. Since gases containing both $^{12}CO_2$ and $^{13}CO_2$ are to be measured in this measurement method, the overlap of these spectra should be corrected for preparation of the calibration curves. The calibration curves to be employed in this measurement are subjected to the correction for the overlap of the absorption spectra.

For preparation of the calibration curve for the $^{12}CO_2$ concentration, the $^{12}CO_2$ absorbances for 20 different $^{12}CO_2$ concentrations within a range of about 0% to about 6% are measured. The $^{12}CO_2$ concentrations and the $^{12}CO_2$ absorbances are plotted as abscissa and ordinate, respectively, as shown in FIG. 17A.

The curve, which passes through the respective data points, is determined by the method of least squares. An approximate quadratic curve includes the least error. Therefore, the approximate quadratic curve is employed as the calibration curve for $^{12}CO_2$ in this embodiment.

In turn, five data points are selected which are located around the $^{12}CO_2$ concentration of the base gas previously determined on the basis of the calibration curve for $^{12}CO_2$. The five data points fall within a concentration range of 1.5%, which accounts for 25% of the entire concentration range (6%) of the calibration curve shown in FIG. 17A. Then, the data within the limited concentration range are used for the preparation of a new calibration curve (see FIG. 17B). It is confirmed that the preparation of the calibration curve within the limited data range improves the conformity of the data to the approximate curve, thereby remarkably reducing errors associated with the preparation of the calibration curve. The $^{12}CO_2$ concentration of the base gas is determined on the basis of the absorbance $^{12}Abs(B)$ of the base gas by using the new calibration curve for $^{12}CO_2$.

The $^{12}CO_2$ concentration of the sample gas is determined in the same manner.

For preparation of the calibration curve for the $^{13}CO_2$ concentration, the $^{13}CO_2$ absorbances for 20 different $^{13}CO_2$ concentrations within a range of about 0.00% to about 0.07% are measured. The $^{13}CO_2$ concentrations and the $^{13}CO_2$ absorbances are plotted as abscissa and ordinate, respectively, as shown in FIG. 18A.

The curve, which passes through the respective data points, is determined by the method of least squares. An approximate quadratic curve includes the least error. Therefore, the approximate quadratic curve is employed as the calibration curve for $^{13}CO_2$ in this embodiment.

In turn, five data points are selected which are located around the $^{13}CO_2$ concentration of the base gas previously determined on the basis of the calibration curve for $^{13}CO_2$. The five data points fall within a concentration range of 0.015%, which accounts for about ¼ of the entire concentration range (0.07%) of the calibration curve shown in FIG. 18A. Then, the data within the limited concentration range are used for the preparation of a new calibration curve (see FIG. 18B). It is confirmed that the preparation of the calibration curve within the limited data range improves the conformity of the data to the approximate curve, thereby remarkably reducing errors associated with the preparation of the calibration curve. The $^{13}CO_2$ concentration of the base gas is determined on the basis of the absorbance $^{13}Abs(B)$ of the base gas by using the new calibration curve for $^{13}CO_2$.

The $^{13}CO_2$ concentration of the sample gas is determined in the same manner.

The $^{12}CO_2$ concentration and $^{13}CO_2$ concentration of the base gas are represented by $^{12}Conc(B)$ and $^{13}Conc(B)$, respectively. The $^{12}CO_2$ concentration and $^{13}CO_2$ concentration of the sample gas are represented by $^{12}Conc(S)$ and $^{13}Conc(S)$, respectively.

IV-4. Calculation of Concentration Ratios

The concentration ratio of $^{13}CO_2$ to $^{12}CO_2$ is determined. The concentration ratios in the base gas and in the sample gas are expressed as $^{13}Conc(B)/^{12}Conc(B)$ and $^{13}Conc(S)/^{12}Conc(S)$, respectively.

Alternatively, the concentration ratios in the base gas and in the sample gas may be defined as $^{13}Conc(B)/\,^{12}Conc(B)+$ $^{13}$Conc(B) and $^{13}$Conc(S)/$^{12}$Conc(S)+$^{13}$Conc(S), respectively. Since the $^{12}CO_2$ concentration is much higher than the $^{13}CO_2$ concentration, the concentration ratios expressed in the former way and in the latter way are substantially the same.

IV-5a. Correction of Concentration Ratios

As described in "BACKGROUND ART", the concentration ratios obtained in the aforesaid manner deviate from actual concentrations, depending on the $^{12}CO_2$ concentration.

Although the cause of the deviation has not been elucidated yet, the deviation supposedly results from changes in the spectroscopic characteristics such as reflectance, refractive index and stray light in dependence on the $^{12}CO_2$ concentration and from the error characteristics of the least square method employed for preparation of the calibration curves.

If the concentration ratio is determined without correcting the deviation, a critical error may result. Therefore, absorbances $^{12}$Abs and $^{13}$Abs of $^{12}CO_2$ and $^{13}CO_2$ in gaseous samples having the same concentration ratio but different $^{12}CO_2$ concentrations are measured, and the $^{13}CO_2$ and $^{12}CO_2$ concentrations and $^{13}CO_2$ concentration ratios of the gaseous samples are determined by using the calibration curves. Then, the $^{12}CO_2$ concentrations $^{12}$Conc and the concentration ratios $^{13}$Conc/$^{12}$Conc are plotted as abscissa and ordinate, respectively.

Figure 1:
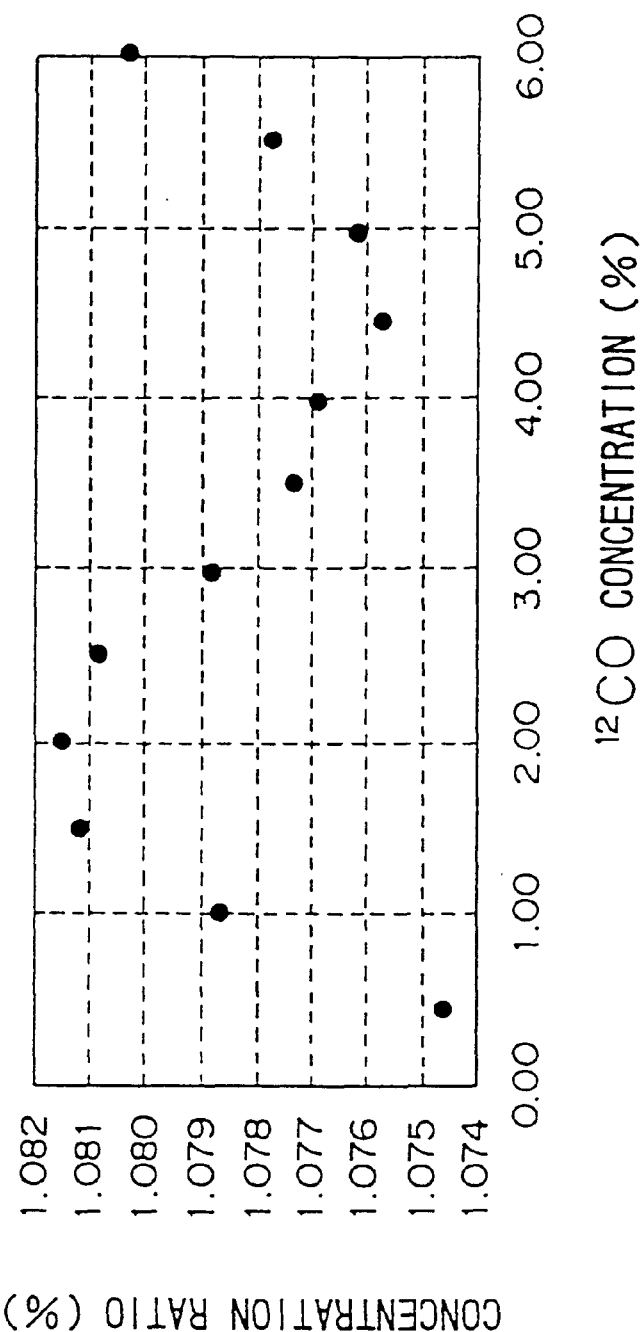
FIG. 1 is a prior art graphical representation in which concentrations $^{12}$Conc and concentration ratios $^{13}$Conc/$^{12}$Conc are plotted as abscissa and ordinate, respectively, the concentrations $^{12}$Conc and $^{13}$Conc and the concentration ratios $^{13}$Conc/$^{12}$Conc having been determined by using calibration curves prepared on the basis of measurements of the absorbances $^{12}$Abs and $^{13}$Abs of component gases in gaseous samples having the same concentration ratio $^{13}$Conc/$^{12}$Conc but different concentrations of the component gases.

The result is shown in FIG. 1.

Figure 19:
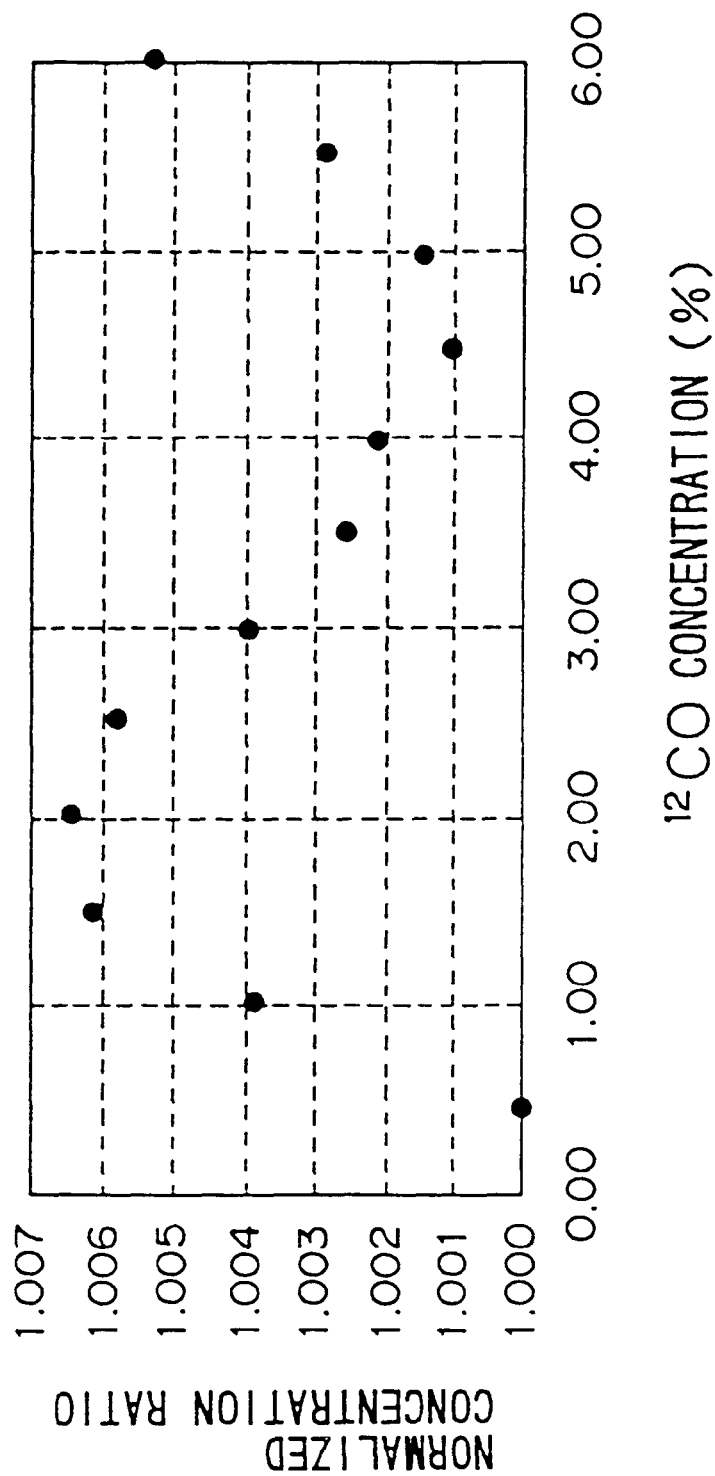
FIG. 19 is a graphical representation in which concentration ratios $^{13}Conc/^{12}Conc$ plotted as ordinate are normalized on the basis of a concentration ratio $^{13}Conc/^{12}Conc$ obtained when $^{12}Conc$ is 0.5%.

The concentration ratios plotted as ordinate in the graph of FIG. 1 are not normalized. The concentration ratios may be normalized for easy processing of data. FIG. 19 illustrates a graph obtained by way of standardization of the concentration ratios in which a concentration ratio in a gaseous sample of the lowest $CO_2$ concentration is regarded as "1". (The concentration ratios thus normalized are hereinafter referred to as "normalized concentration ratios".)

To obtain an approximate curve accommodating these plotted data, the method of least squares is employed for approximation of the data. It is experientially known that a function of the fourth degree expressed by the following equation (1) provides the most accurate approximate curve.

$$F(x)=ax^4+bx^3+cx^2+dx+e \quad (1)$$

wherein F is a normalized concentration ratio, a to d are coefficients, e is a constant, and x is a $^{12}CO_2$ concentration. Therefore, the fourth-order function (1) is used as a correction equation. Alternatively, a spline function may be used.

Standardized $^{13}CO_2/^{12}CO_2$ concentration ratios are calculated from the correction equation (1) on the basis of the $^{12}CO_2$ concentrations $^{12}$Conc(B) and $^{12}$Conc(S) in the breath samples of the patient. Then, the concentration ratios $^{13}$Conc(B)/$^{12}$Conc(B) and $^{13}$Conc(S)/$^{12}$Conc(S) of the base gas and the sample gas obtained in the measurement are respectively divided by the normalized concentration ratios calculated from the correction equation (1). Thus, corrected concentration ratios are obtained as follows:

Corrected concentration ratio=$^{13}$Conc(B)/[$^{12}$Conc(B)·F($^{12}$Conc(B))]

Corrected concentration ratio=$^{13}$Conc(S)/[$^{12}$Conc(S)·F($^{12}$Conc(S))]

IV-5b. Correction of Concentration Ratios

The $^{13}CO_2$ concentration ratios of the base gas and the sample gas are subjected to a correction for oxygen concentration according to the present invention.

The $^{13}CO_2$ concentration ratios are corrected by using a graph (FIG. 2) in which measurements of the $^{13}CO_2$ concentration ratio are plotted with respect to the oxygen contents of gaseous samples.

Figure 2:
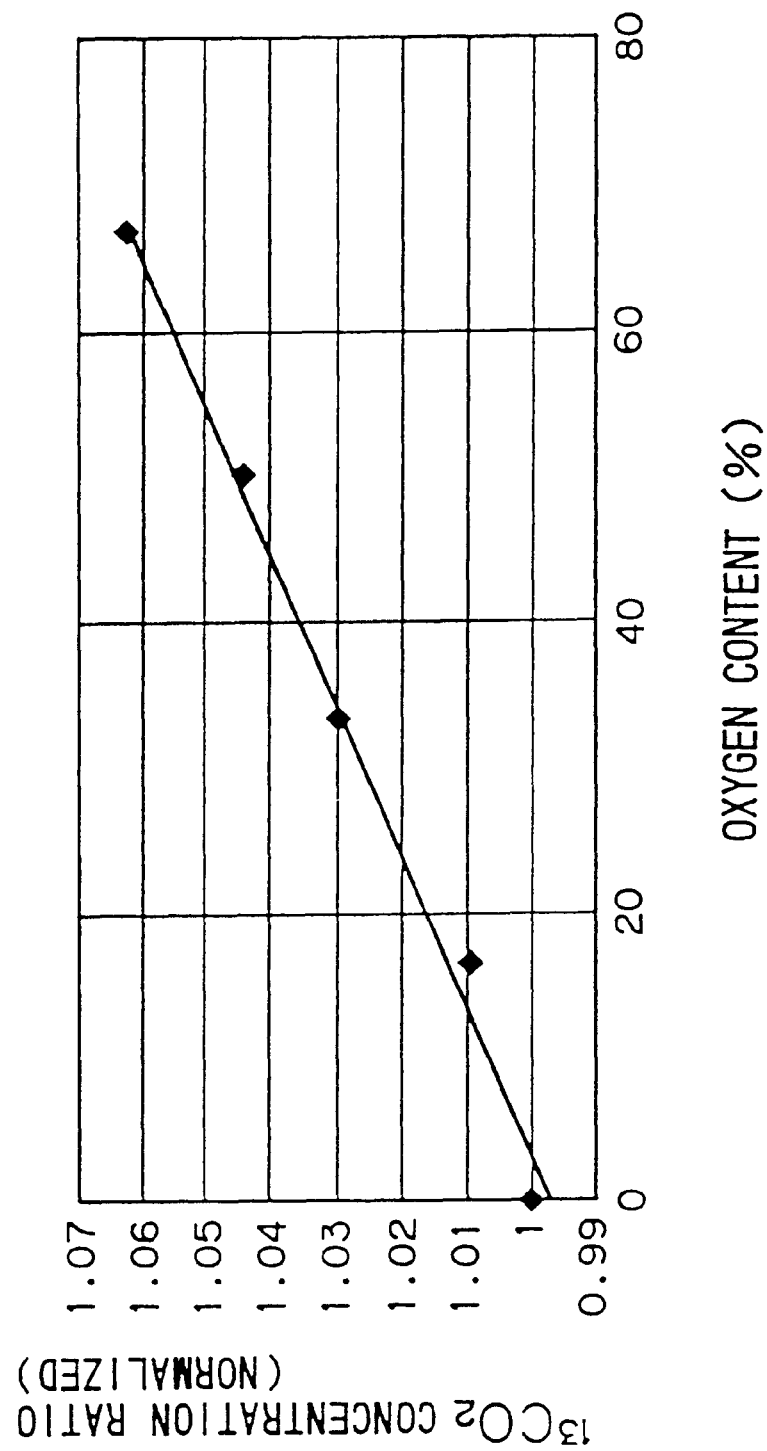
FIG. 2 is a prior art graphical representation in which $^{13}CO_2$ concentration ratios are plotted with respect to oxygen contents, the $^{13}CO_2$ concentration ratios having been determined by measuring gaseous samples containing $^{13}CO_2$ diluted with oxygen and nitrogen and having the same $^{13}CO_2$ concentration ratio but different oxygen concentrations, the $^{13}CO_2$ Qoncentration ratios being normalized on the basis of a $^{13}CO_2$ concentration ratio for an oxygen content of 0%.
Figure 3:
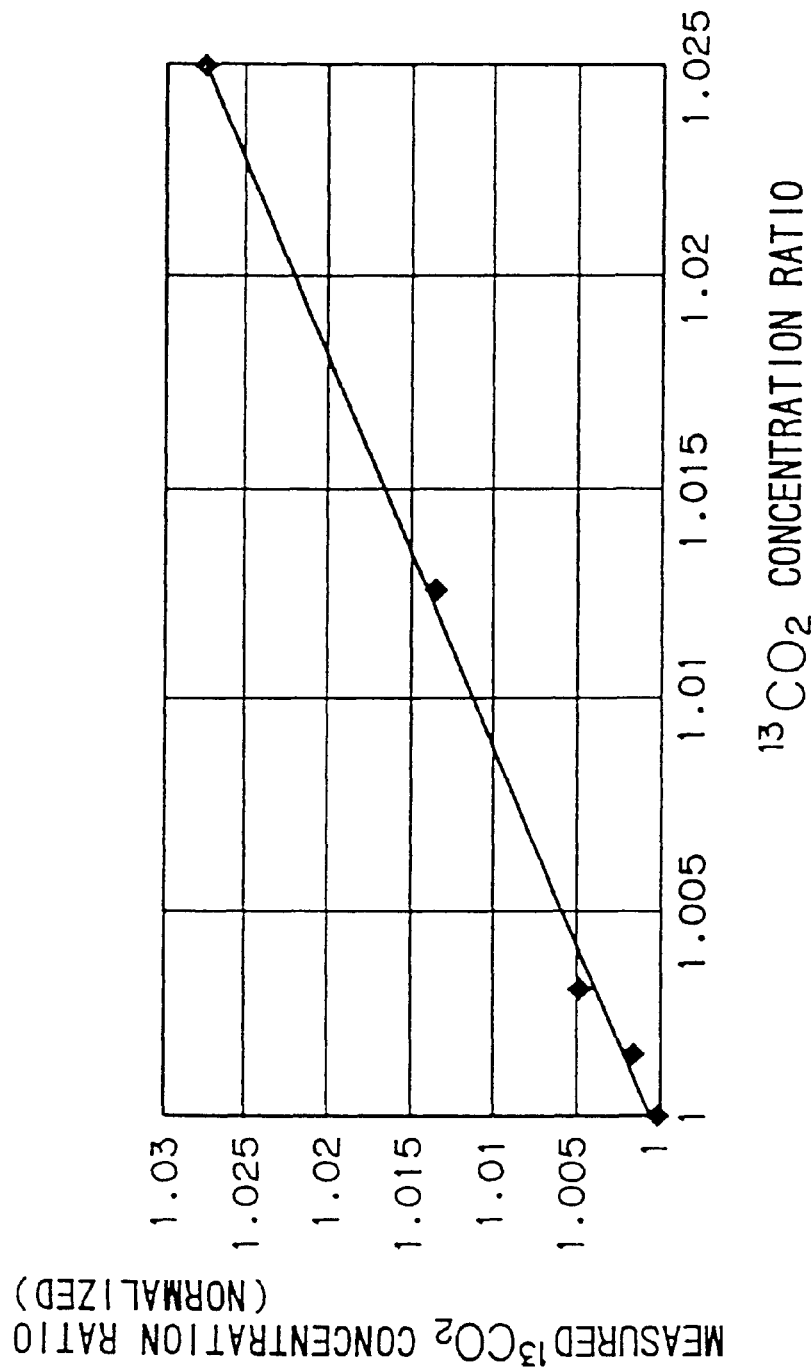
FIG. 3 is a prior art graphical representation illustrating the result of measurement in which gaseous samples having different $^{13}CO_2$ concentration ratios and containing no oxygen were measured, in which graphical representation the actual $^{13}CO_2$ concentration ratios and the measured $^{13}CO_2$ concentration ratios are plotted as abscissa and ordinate, respectively, and the $^{13}CO_2$ concentration ratios are normalized on the basis of the minimum $^{13}CO_2$ concentration ratio.

More specifically, normalized $^{13}CO_2$ concentration ratios are obtained from the graph shown in FIG. 2 on the basis of the concentrations of oxygen in the breath samples which are measured by means of the $O_2$ sensor. Then, the $^{13}CO_2$ concentration ratios of the base gas and the sample gas are respectively divided by the normalized $^{13}CO_2$ concentration ratios. Thus, the $^{13}CO_2$ concentration ratios corrected depending on the oxygen concentrations can be obtained.

IV-6. Determination of Change in $^{13}C$

A difference in $^{13}C$ between the sample gas and the base gas is calculated from the following equation:

$\Delta^{13}C$=[Concentration ratio of sample gas–Concentration ratio of base gas]$\times 10^3$/[Concentration ratio of base gas]

(Unit: per mill)

V. Modification

The present invention is not limited to the embodiment described above. In the above-mentioned embodiment, the $^{12}CO_2$ and $^{13}CO_2$ concentrations of the base gas and the sample gas are determined, then the concentration ratios thereof are calculated, and the concentration ratios are subjected to the oxygen concentration correction. Alternatively, the concentration ratios may be determined after the $^{12}CO_2$ and $^{13}CO_2$ concentrations of the base gas and the sample gas are determined and the $^{12}CO_2$ and $^{13}CO_2$ concentrations are corrected by way of the oxygen concentration correction.

VI. Experiments

VI-1

The absorbances of gaseous samples respectively containing $^{12}CO_2$ in concentrations $^{12}$Conc of 1%, 2%, 3%, 4%, 5% and 6% with a concentration ratio $^{13}$Conc/$^{12}$Conc of 1.077% were measured in accordance with the method for spectrometrically measuring an isotopic gas. The $^{12}CO_2$ concentrations $^{12}$Conc and $^{13}CO_2$ concentrations $^{13}$Conc of the gaseous samples were determined on the basis of the measured absorbances by using the calibration curves. The $^{12}CO_2$ concentrations $^{12}$Conc and the concentration ratios $^{13}$Conc/$^{12}$Conc were plotted as abscissa and ordinate, respectively, as shown in FIG. 20.

The maximum and minimum values of the concentration ratios $^{13}$Conc/$^{12}$Conc were 1.083% and 1.076%, respectively, and the difference therebetween was 0.007%.

Figure 21:
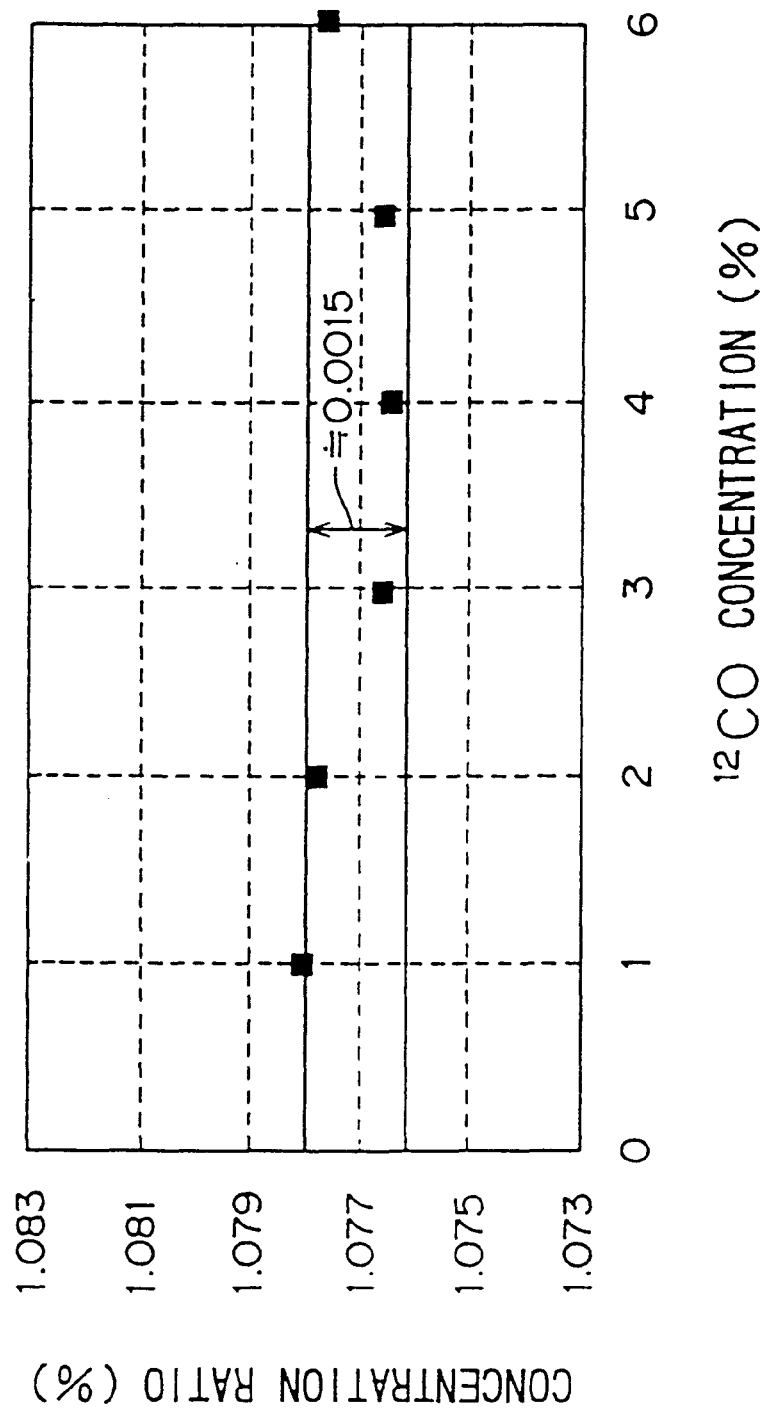
FIG. 21 is a graphical representation illustrating the relationship of $^{12}Conc$ (plotted as abscissa) versus concentration ratio $^{13}Conc/^{12}Conc$ (plotted as ordinate) which was determined by measuring the $^{12}CO_2$ concentrations $^{12}Conc$ and $^{13}CO_2$ concentrations $^{13}Conc$ of gaseous samples and correcting obtained concentration ratios $^{13}Conc/^{12}Conc$.

In turn, the concentration ratios $^{13}$Conc/$^{12}$Conc were corrected by using the correction equation (1), thus providing a less undulant curve as shown in FIG. 21. In FIG. 21, the maximum and minimum values of the concentration ratios $^{13}$Conc/$^{12}$Conc were 1.078% and 1.076%, respectively, and the difference therebetween was 0.0015%.

Therefore, the correction with the correction equation (1) remarkably reduced the variation in the concentration ratio $^{13}$Conc/$^{12}$Conc.

VI-2

The absorbances of gaseous samples respectively containing $^{12}CO_2$ in concentrations $^{12}$Conc of 1%, 2%, 3%, 4%, 5% and 6% with a concentration ratio $^{13}$Conc/$^{12}$Conc of 1.065% were measured in accordance with the method for spectrometrically measuring an isotopic gas. The $^{12}$Conc and the $^{13}$Conc were determined on the basis of the measured absorbances by using the calibration curves shown in FIGS. 17A and 18A. The $^{12}CO_2$ concentrations $^{12}$Conc and the concentration ratios $^{13}$Conc/$^{12}$Conc were plotted as abscissa and ordinate, respectively, as shown in FIG. 22.

The maximum and minimum values of the concentration ratios $^{13}$Conc/$^{12}$Conc were 1.077% and 1.057%, respectively, and the difference therebetween was 0.02%.

In turn, concentration ratios $^{13}$Conc/$^{12}$Conc were determined by using the calibration curves shown in FIGS. 17A and 18A and then using the limited-range calibration curves shown in FIGS. 17B and 18B, thus providing a less undulant curve as shown in FIG. 23. In FIG. 23, the maximum and minimum values of the concentration ratios $^{13}$Conc/$^{12}$Conc were 1.066% and 1.064%, respectively, and the difference therebetween was 0.002%.

Therefore, the method of the present invention, in which the calibration curves were produced again, remarkably reduced the variation in the concentration ratio $^{13}$Conc/$^{12}$Conc.

IV-3

The absorbances of gaseous samples having different known $^{13}CO_2$ concentration ratios and containing various concentration of oxygen (up to 90%) were measured, and then the $^{13}CO_2$ concentration ratios were determined on the basis of the measured absorbances by using the calibration curves. Further, the $^{13}CO_2$ concentration ratios thus determined were corrected by using a correction line as shown in FIG. 2.

accordance with the prior art method B in which the absorbance of $^{12}CO_2$ in the sample gas was determined on the basis of a value obtained in the reference measurement only before the sample gas measurement.

The results of the calculation of the concentrations in accordance with the method A are shown in Table 1. In Table 1, the concentrations obtained in the second and subsequent measurements were normalized by regarding a concentration obtained in the first measurement as "1". The standard deviation of the concentration data calculated in accordance with the method A was 0.0009.

TABLE 1

| 1 | 2 | 3 | 4 | 5 | 6 | 7 | 8 | 9 | 10 |
|---|---|---|---|---|---|---|---|---|----|
| 1 | 1.0011 | 0.9996 | 0.9998 | 1.0011 | 0.9982 | 1 | 1.0014 | 1.0005 | 1.0006 |

The results of the calculation of the concentrations in accordance with the method B are shown in Table 2. In Table 2, the concentrations obtained in the second and subsequent measurements were normalized by regarding a concentration obtained in the first measurement as "1". The standard deviation of the concentration data calculated in accordance with the method B was 0.0013.

TABLE 2

| 1 | 2 | 3 | 4 | 5 | 6 | 7 | 8 | 9 | 10 |
|---|---|---|---|---|---|---|---|---|----|
| 1 | 1.0024 | 1.0001 | 0.9996 | 1.0018 | 0.9986 | 1 | 1.0022 | 1.0014 | 1.0015 |

Figure 24:
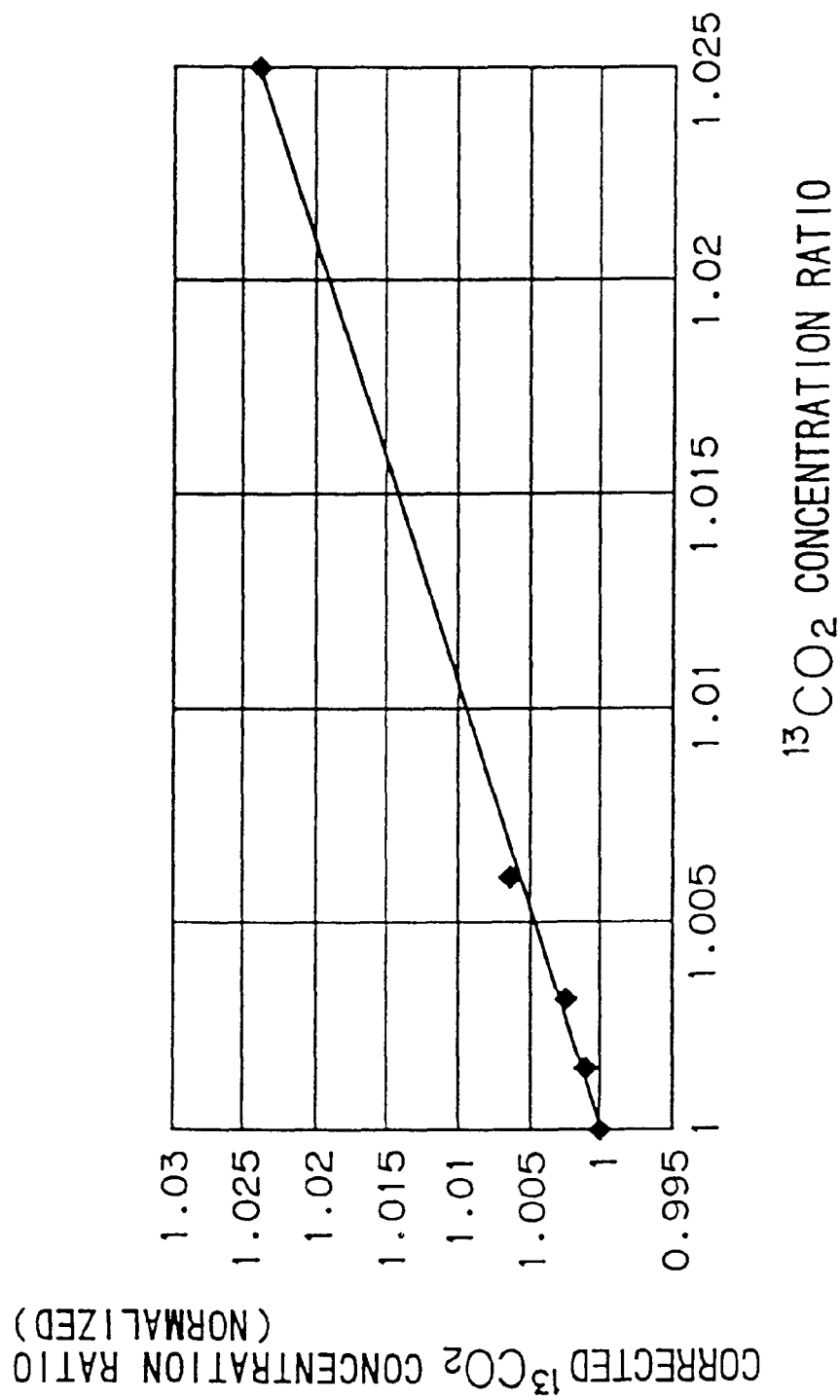
FIG. 24 is a graphical representation illustrating the result of measurement in which gaseous samples having different $^{13}CO_2$ concentration ratios and containing various concentration of oxygen (up to 90%) were measured and measurements were subjected to a correction process according to the present invention, in which graphical representation the actual $^{13}CO_2$ concentration ratios and the measured $^{13}CO_2$ concentration ratios are plotted as abscissa and ordinate, respectively, and the $^{13}CO_2$ concentration ratios are normalized on the basis of the minimum $^{13}CO_2$ concentration ratio.

The actual $^{13}CO_2$ concentration ratios and the $^{13}CO_2$ concentration ratios thus corrected were normalized, and plotted as abscissa and ordinate, respectively, as shown in FIG. 24.

Figure 4:
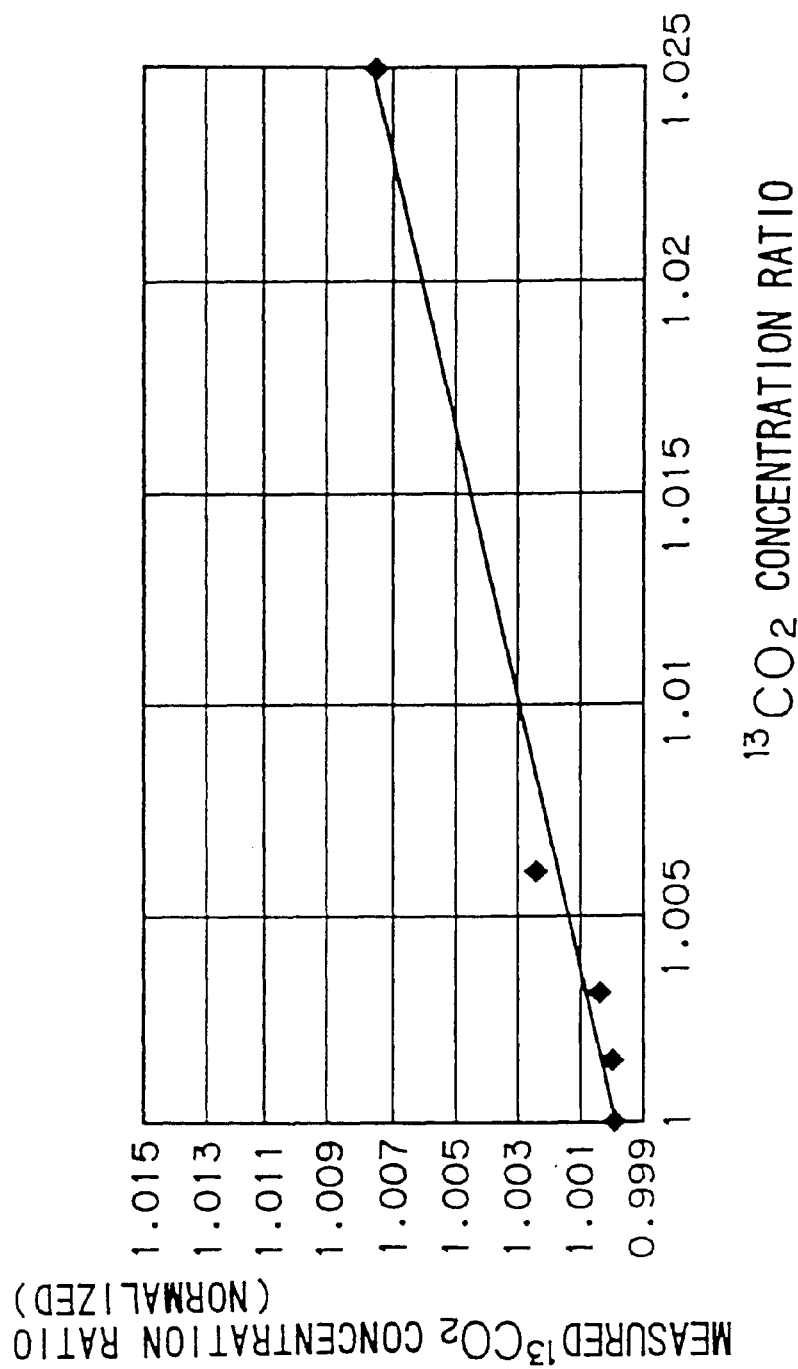
FIG. 4 is a prior art graphical representation illustrating the result of measurement in which gaseous samples having different $^{13}CO_2$ concentration ratios and containing various concentration of oxygen (up to 90%) were measured, in which graphical representation the actual $^{13}CO_2$ concentration ratios and the measured $^{13}CO_2$ concentration ratios are plotted as abscissa and ordinate, respectively, and the $^{13}CO_2$ concentration ratios are normalized on the basis of the minimum $^{13}CO_2$ concentration ratio.

In FIG. 24, the relationship between the actual $^{13}CO_2$ concentration ratio and the measured $^{13}CO_2$ concentration ratio is about 1:1 (or the scope of the fitting curve in FIG. 24 is about 1). In comparison with the prior art shown in FIG. 4, in which the relationship between the actual $^{13}CO_2$ concentration ratio and the measured $^{13}CO_2$ concentration ratio is about 1:0.3 (or the scope of the fitting curve is about 0.3), the measurement accuracy was drastically improved by performing the correction.

Thus, the correction using the correction line remarkably improved the accuracy of the measurement of the $^{13}CO_2$ concentration ratio.

VI-4

The $^{12}CO_2$ concentration of the same sample gas containing carbon dioxide was measured a plurality of times by means of the apparatus for spectrometrically measuring an isotopic gas.

After one hour warming-up of apparatus, a measuring procedure consisting of the reference gas measurement, the sample gas measurement, the reference gas measurement, the sample gas measurement and the reference gas measurement were performed ten times on the same sample gas. The $^{12}CO_2$ concentration was determined in each cycle of the measuring procedure in accordance with the method A of the present invention in which the absorbance of $^{12}CO_2$ in the sample gas was determined on the basis of an average of values obtained in the reference gas measurements performed before and after the sample gas measurement, and in As can be understood from the foregoing, the method of the present invention, in which the absorbances are determined on the basis of the light intensity measured on the sample gas and an average of the light intensity measured on the reference gas, provides concentration data with little variation.

What is claimed is:

1. A method for spectrometrically measuring an isotopic gaseous test sample containing a plurality of component gases including $^{12}CO_2$ and $^{13}CO_2$, by measuring intensity of light transmitted through the gaseous test sample at wavelengths suitable for the respective component gases, and processing data of the light intensity to determine concentrations of the component gases in the gaseous test sample, the method comprising: a first step of introducing the gaseous test sample into a cell and measuring absorbances of the respective component gases in the gaseous test sample; a second step of determining concentrations and concentration ratios of the component gases in the gaseous test sample on the basis of calibration curves; and a third step of obtaining concentration ratio correction values for the component gases on the basis of the concentrations of the component gases obtained in the second step by using correction curves preliminary prepared by measuring absorbances of the component gases in gaseous samples containing the respective component gases in known concentrations with known concentration ratios, determining concentrations and concentration ratios of the component gases in the gaseous samples on the basis of the calibration curves, and by plotting the thus determined concentrations and concentration ratios of the component gases in the gaseous samples, and respectively dividing the concentration ratios of the component gases obtained in the second step by the concentration ratio correction values for the component gases, thereby correcting the concentration ratios of the component gases in the gaseous test sample.

2. A method as set forth in claim 1, wherein the correction curves prepared in the third step are approximate fourth-order curves respectively representing the relationships between the concentrations and concentration ratios of the component gases in the gaseous samples determined in the third step.

3. A method for spectrometrically measuring an isotopic gas by introducing a gaseous test sample containing a plurality of component gases including $^{12}CO_2$ and $^{13}CO_2$ into a cell, measuring intensity of light transmitted through the gaseous test sample at wavelengths suitable for the respective component gases, and processing data of the light intensity to determine concentrations of the component gases in the gaseous test sample, the method comprising: a first step of introducing the gaseous test sample into the cell and measuring absorbances of the respective component gases in the gaseous test sample; a second step of preliminarily determining concentrations of the component gases in the gaseous test sample on the basis of calibration curves prepared by using data obtained by measuring gaseous samples respectively containing the component gases in known concentrations within a predetermined range; and a third step of preparing new calibration curves by using some of the data within limited ranges around the concentrations of the component gases in the gaseous test sample preliminarily determined in the second step, and determining concentrations of the component gases in the gaseous test sample by using the calibration curves thus prepared.

4. A method for spectrometrically measuring an isotopic gas by introducing a gaseous test sample containing $^{13}CO_2$ into a cell, measuring an intensity of light transmitted through the gaseous test sample at a wavelength suitable for $^{13}CO_2$, and processing data of the light intensity to determine a concentration of $^{13}CO_2$ in the gaseous test sample, the method comprising: a first step of introducing the gaseous test sample into the cell and measuring an absorbance of $^{13}CO_2$ in the gaseous test sample; a second step of determining a concentration of $^{13}CO_2$ in the gaseous test sample on the basis of a calibration curve; and a third step of measuring an oxygen concentration in the gaseous test sample, obtaining a concentration correction value for $^{13}CO_2$ on the basis of a correction curve and the measured oxygen concentration, said correction curve being preliminary prepared by measuring absorbances of $^{13}CO_2$ in gaseous samples containing $^{13}CO_2$ and oxygen in known concentrations, determining concentrations of $^{13}CO_2$ in the gaseous samples on the basis of the calibration curve, and by plotting the concentrations of $^{13}CO_2$ thus determined with respect to the oxygen concentrations, and dividing the concentration of $^{13}CO_2$ obtained in the second step by the concentration correction value for $^{13}CO_2$ determined on the basis of the correction curve, thereby correcting the concentration of $^{13}CO_2$ in the gaseous test sample.

5. A method for spectrometrically measuring an isotopic gas by introducing a gaseous test sample containing $^{12}CO_2$ and $^{13}CO_2$ into a cell, measuring intensity of light transmitted through the gaseous test sample at wavelengths suitable for $^{12}CO_2$ and $^{13}CO_2$, and processing data of the light intensity to determine concentrations of or a concentration ratio between $^{13}CO_2$ and $^{12}CO_2$ in the gaseous test sample, the method comprising: a first step of introducing the gaseous test sample into the cell and measuring absorbances of $^{12}CO_2$ and $^{13}CO_2$ in the gaseous test sample; a second step of determining concentrations of or a concentration ratio between $^{13}CO_2$ and $^{12}CO_2$ in the gaseous test sample on the basis of calibration curves; and a third step of measuring an oxygen concentration in the gaseous test sample, obtaining concentration correction values or a concentration ratio correction value for $^{13}CO_2$ and $^{12}CO_2$ on the basis of correction curves and the measured oxygen concentration, said correction curves being preliminary prepared by measuring absorbances of $^{12}CO_2$ and $^{13}CO_2$ in gaseous samples containing $^{12}CO_2$ and $^{13}CO_2$ and oxygen in known concentrations, determining concentrations of or concentration ratios between $^{13}CO_2$ and $^{12}CO_2$ in the gaseous samples on the basis of the calibration curves, and by plotting the concentrations of or the concentration ratios between $^{13}CO_2$ and $^{12}CO_2$ thus determined with respect to the oxygen concentrations, and respectively dividing the concentrations of or the concentration ratio between $^{13}CO_2$ and $^{12}CO_2$ determined in the second step by the concentration correction values or the concentration ratio correction value determined on the basis of the correction curves, thereby correcting the concentrations of or the concentration ratio between $^{13}CO_2$ and $^{12}CO_2$ in the gaseous test sample.

6. A method for spectrometrically measuring an isotopic gas by introducing a gaseous test sample containing $^{12}CO_2$ and $^{13}CO_2$ as component gases into a cell, measuring absorbances of light transmitted through the gaseous test sample at wavelengths suitable for the respective component gases, and determining concentrations of the respective component gases on the basis of calibration curves prepared by measuring gaseous samples respectively containing the component gases in known concentrations, the method comprising: measuring two gaseous test samples obtained from one body and, if a concentration of $^{12}CO_2$ in one of the two gaseous test samples is higher than a concentration of $^{12}CO_2$ in the other gaseous test sample, diluting said one gaseous test sample to a $^{12}CO_2$ concentration level equivalent to that of the other gaseous test sample, and then determining $^{13}CO_2/^{12}CO_2$ concentration ratios in the respective gaseous test samples.

7. A method as set forth in claim 6, further comprising a preliminary measurement and a main measurement, wherein concentrations of $CO_2$ in first and second gaseous test samples obtained from one body are respectively measured in the preliminary measurement and, if the measured concentration of $CO_2$ in the first gaseous test sample is higher than the measured concentration of $CO_2$ in the second gaseous test sample, the first gaseous test sample is diluted to a $CO_2$ concentration level equivalent to that of the second gaseous test sample, then a $^{13}CO_2/^{12}CO_2$ concentration ratio in the first gaseous test sample thus diluted is determined and a $^{13}CO_2/^{12}CO_2$ concentration ratio in the second gaseous test sample is determined in the main measurement.

8. A method as set forth in claim 6, further comprising a preliminary measurement and a main measurement, wherein concentrations of $CO_2$ in first and second gaseous test samples obtained from one body are respectively measured in the preliminary measurement, and if the measured concentration of $CO_2$ in the first gaseous test sample is lower than the measured concentration of $CO_2$ in the second gaseous test sample, a $^{13}CO_2/^{12}CO_2$ concentration ratio in the first gaseous test sample is determined, then the second gaseous test sample is diluted to a $CO_2$ concentration level equivalent to that of the first gaseous test sample, and a $^{13}CO_2/^{12}CO_2$ concentration ratio in the second gaseous test sample thus diluted is determined in the main measurement.

9. An apparatus for spectrometrically measuring an isotopic gas by determining concentrations of a plurality of component gases $^{12}CO_2$ and $^{13}CO_2$ in a gaseous test sample, the apparatus comprising: a cell for receiving the gaseous test sample; means for transmitting light through the gaseous test sample received in the cell; means for measuring intensity of light transmitted through the gaseous test sample at wavelengths suitable for the respective component gases, and processing data of the light intensity; and gas injection means for sucking the gaseous test sample thereinto and then mechanically pushing out the gaseous test sample into the cell at a constant rate during measurement of light intensity.

10. An apparatus as set forth in claim 9, further comprising temperature maintaining means for maintaining the cell receiving the gaseous test sample introduced therein at a constant temperature.

11. An apparatus for spectrometrically measuring an isotopic gas which is adapted to determine concentrations of a plurality of component gases in a gaseous test sample by introducing the gaseous test sample into a cell, then measuring intensity of light transmitted through the gaseous test sample at wavelengths suitable for the respective component gases and processing data of the light intensity, comprising: means for positioning the cell receiving the gaseous test sample introduced therein in the light path between a light source and a photoreceptor; a reference cell filled with a reference gas having no absorption at the wavelengths for measurement is disposed in a portion of the light path not occupied by the cell; and gas flow generating means for constantly passing the reference gas through the reference cell at a constant flow rate.

12. An apparatus as set forth in claim 11, further comprising temperature maintaining means for maintaining the cell receiving the gaseous test sample introduced therein and the reference cell at a constant temperature.

13. An apparatus for spectrometrically measuring an isotopic gas which is adapted to determine concentrations of a plurality of component gases in a gaseous test sample by introducing the gaseous test sample into two cells, then measuring intensity of light transmitted through the gaseous test sample at wavelengths suitable for the respective component gases and processing data of the light intensity, comprising: means for orienting the two cells for receiving the gaseous test sample introduced therein in parallel along light paths between a light source and a photoreceptor, the two cells having different lengths; a reference cell filled with a reference gas having no absorption at the wavelengths for measurement disposed between a shorter one of the two cells and the photoreceptor or between the light source and the shorter cell; and gas flow generating means for constantly passing the reference gas through the reference cell at a constant flow rate.

14. An apparatus as set forth in claim 13, further comprising temperature maintaining means for maintaining the cells receiving the gaseous test sample introduced therein and the reference cell at a constant temperature.

* * * * *

UNITED STATES PATENT AND TRADEMARK OFFICE
CERTIFICATE OF CORRECTION

PATENT NO.   : 6,274,870 B1
DATED        : August 14, 2001
INVENTOR(S)  : Yasuhiro Kubo, Katsuhiro Morisawa, Yasushi Zasu, Eiji Ikegami, Kazunori Tsutsui, Tamotsu Hamao, Masaaki Mori, Takashi Maruyama It is certified that error appears in the above-identified patent and that said Letters Patent is hereby corrected as shown below:

<u>Title page,</u>
Item [62], Division of application No. 08/849,351, filed as application No. PCT/JP96/02876 on "Oct. 21, 1996" to read -- Oct. 2, 1996. --

Signed and Sealed this

Second Day of April, 2002

Attest:

JAMES E. ROGAN
*Attesting Officer*     *Director of the United States Patent and Trademark Office*